United States Patent
Fraker et al.

(10) Patent No.: US 6,630,154 B1
(45) Date of Patent: *Oct. 7, 2003

(54) POLYMER FORMULATIONS CONTAINING PERFLUORINATED COMPOUNDS FOR THE ENGINEERING OF CELLS AND TISSUES FOR TRANSPLANTATION THAT IMPROVES CELL METABOLISM AND SURVIVAL, AND METHODS FOR MAKING SAME

(75) Inventors: Christopher Fraker, Hollywood, FL (US); Luca Inverardi, Miami Beach, FL (US); Marcos Mares-Guia, Miami, FL (US); Camillo Ricordi, Miami Beach, FL (US)

(73) Assignees: Biomm, Inc., Miami, FL (US); Diabetes Research Institute, University of Miami, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/477,466

(22) Filed: Jan. 4, 2000

Related U.S. Application Data

(60) Provisional application No. 60/114,708, filed on Jan. 4, 1999.

(51) Int. Cl.[7] .................. A61F 2/02; A61K 31/734; A61K 31/726
(52) U.S. Cl. ............... 424/423; 424/443; 424/488; 435/1.1; 435/1.2; 514/54; 514/55; 514/56
(58) Field of Search ................ 514/54, 55, 56; 424/423, 443, 488; 435/1.1, 1.2

(56) References Cited

U.S. PATENT DOCUMENTS 5,702,881 A * 12/1997 Brasile .................. 435/1.2
6,281,341 B1 * 8/2001 Mares-Guia ............ 536/3

* cited by examiner

*Primary Examiner*—James O. Wilson
*Assistant Examiner*—Leigh C Maier
(74) *Attorney, Agent, or Firm*—Frommer Lawrence & Haug LLP; Grace L. Pan

(57) ABSTRACT

Disclosed and claimed are: a composition including at least one glycosaminoglycan, e.g., CIS, at least one perfluorinated substance and at least one alginate, e.g., sodium alginate, wherein:

the at least one glycosaminoglycan and/or the perfluorinated substance and/or the alginate are cross-linked or polymerized, e.g., the alginate is cross-linked or polymerized, for instance by addition of an inorganic salt, such as a calcium salt; or the at least one glycosaminoglycan, the perfluorinated substance and the alginate are covalently bound, e.g., by means of a coupling reaction involving a linker molecule such as DVS; or the at least one glycosaminoglycan and/or the perfluorinated substance and/or the alginate are cross-linked or polymerized, e.g., the alginate is cross-linked or polymerized, for instance by addition of an inorganic salt, such as a calcium salt, and the at least one glycosaminoglycan and the alginate are covalently bound, e.g., by means of a coupling reaction involving a linker molecule such as DVS, and the covalent binding can have been performed prior to cross-linking or polymerizing or vice versa; and, gels comprising the composition; mixtures of such gels or of at least one such gel and at least one such composition; and, methods for making and using such compositions and gels, including products therefrom such as "paints", sprays, matrices, beads, microcapsules.

7 Claims, 3 Drawing Sheets

(3 of 3 Drawing Sheet(s) Filed in Color)

POLYMER FORMULATIONS CONTAINING PERFLUORINATED COMPOUNDS FOR THE ENGINEERING OF CELLS AND TISSUES FOR TRANSPLANTATION THAT IMPROVES CELL METABOLISM AND SURVIVAL, AND METHODS FOR MAKING SAME

CROSS REFERENCE TO RELATED APPLICATIONS

This application claims priority to provisional application serial No. 60/114,708, filed Jan. 4, 1999 entitled "Novel Polymer Formulations For the Engineering of Cells and Tissues for Transplantation That Improves Cell Metabolism and Survival, And Methods for Making Same" incorporated herein by reference, together with any documents therein cited and any documents cited or referenced in therein cited documents. Reference is also made to U.S. patent application Ser. No. 08/417,652 filed Apr. 5, 1995, now U.S. Pat. No. 5,808,050 issued Sep. 15, 1998, and to U.S. application Ser. No. 08/877,682, filed Jun. 17, 1997, now U.S. Pat. No. 6,281,341 issued Aug. 28, 2001, and to WO98/49202, each of which is hereby incorporated herein by reference, together with any documents cited therein and any documents cited or referenced in therein cited documents.

FIELD OF THE INVENTION

The greatest obstacle to the field of cell and tissue encapsulation/immunoisolation has historically been the lack of sufficient oxygen and nutrient transport across the polymer membranes used to encapsulate cells and tissues. The result of this insufficient gas and nutrient exchange is cell death and lowered metabolic activity. Given that most of these encapsulation devices are used in hormone replacement therapies, such as encapsulated islet cells to treat Diabetes Mellitus, a lowered metabolic activity increases many fold the tissue requirement needed to therapeutically treat the hormone deficiency and, to date, has not generated any devices with clinical applicability to treat the many millions of diabetics throughout the world. The present invention relates to a novel device within which tissue density could be increased and gas and nutrient exchange could be improved thus greatly benefit the field of immunoisolation.

After nearly thirty years of extensive research in the field of islet cell encapsulation, most of the primary contributors in this specialized area agree upon three important tenets (See References cited 1 to 19). First, that in any geometrical style of immunoisolation device, no one dimension can exceed a value of 1 mm. Second, that no device can be loaded with cells at a tissue density higher than 5–10% v/v. Third, regardless of matrix structure, diffusion of metabolites into and insulin out of such devices is often delayed and is governed by simple diffusion gradients across the distance between the cells and the periphery of the capsule. The end results of such limitations are numerous. First, in order to achieve clinical success with any such devices, the ratio of polymer to tissue that would need to be transplanted into a diabetic patient of average weight would rapidly fill the intraperitoneal cavity of a transplant recipient. Second, if any of the above outlined tenets are modified, the result is often catastrophic to the encapsulated islets. The incidence of graft failure increases dramatically, with subclinical performances in functional tests, and the evidence of device-wide cell necrosis is prevalent upon post-explant histological examination. The primary cause for these results is frequently confirmed as the hypoxic environment of isolated and further, immunoisolated islet cells. Given the increased metabolic demands of islet cells in comparison to other somatic cells, the need for improving their oxygen supply after isolation, immunoisolation, and transplantation is of the utmost importance to the possibility of such devices having clinical relevance.

Colton and another group under Per-Ola Carlsson have implemented microelectrodes to measure oxygen partial pressures within islets, in their native environment, after isolation, and post-transplant in polymer devices and free, under the kidney capsule. Both groups found similarly (See references cited 19 and 20). The oxygen partial pressures in the native pancreatic islets are the highest of any organ within the body, measuring 37–46 mmHg (compare this to the value of 13–21 mmHg for cells within the renal cortex). Upon isolation, these values fall between 14–19 mm Hg. Upon transplantation in normoglycemic animals under the kidney capsule, the values fall slightly to 9–15 mmHg. If transplanted into severely hyperglycemic animals (above 350 mg/dL) these values fall between 6–8 mmHg. When the cells are immunoisolated and, therefore, do not lend themselves easily to transplant in a vascularized region such as the kidney capsule, the oxygen values drop even further. In fact, in hyperglycemic animals, the oxygen partial pressures of islets within polymer capsules can drop to values as low as 1–2 mmHg. These nearly anoxic conditions can result in quick cell death, particularly the nearer the cell to the core of the polymer device.

The invention further relates to the inclusion of perfluorinated substances in the Biodritin polymer formulations, in order to achieve better oxygen availability for encapsulated cells or tissues. Perfluoro organic compounds are excellent solvents for oxygen, having several fold higher solubility for oxygen than water. These compounds are largely used as blood substitutes and more recently, have been used for tissue preservation after removal from animals, as well as to improve islet isolations from pancreas.

Thus, the invention especially relates to adding perfluorinated substances in the Biodritin heteropolysaccharide, gels therefrom and/or a composition, e.g., solutions having adjustable viscosity, prepared by manipulating the concentration of Biodritin heteropolysaccharide, and/or ion concentrations, e.g., calcium; and/or a gel or sol comprising the Biodritin heteropolysaccharide; the synthesis, purification and utilization of Biodritin heteropolysaccharide as a novel glycopolymer and/or heteropolysaccharide and/or gels, solutions and/or sols comprising Biodritin heteropolysaccharide. Gels are obtained by adding an inorganic ion, such as calcium ions, to Biodritin heteropolysaccharide. Sols can be obtained by treatment of a gel with a suitable agent such as a sodium salt, e.g., citrate salts or ethylene-diamine-tetraacetic (EDTA) as sodium salt. Gels can have varying viscosity by varying the amount of Biodritin heteropolysaccharide and/or inorganic ion, e.g., calcium ion; and with an amount of calcium ions, infinite gels can be obtained.

The invention further relates to adding the perfluorinated substances to a composition herein termed "Biodritin polymer network", and to methods and formulations for preparing a Biodritin polymer network. A Biodritin polymer network can comprise at least one glycosaminoglycan, e.g., chondroitin sulfate-4 and/or 6, and at least one alginic acid salt, e.g., sodium alginate, wherein at least one of the glycosaminoglycan and alginic acid salt is cross-linked. (See U.S. application Ser. No. 08/877,682, now U.S. Pat. No. 6,281,341, filed Jun. 17, 1997 and WO98/49202 with respect to "Biodritin" and "Biodritin Polymer Network"). And, the methods and formulations for preparing a Biodritin polymer network comprises admixing the glycosaminoglycan and alginic acid salt and adding at least one cross-linking agent, e.g., an inorganic ion. For instance, a Biodritin polymer network which is believed, without necessarily wishing to be bound by any one particular theory, to be a semi-interpenetrating polymer network (s-IPN), is formed by addition of inorganic ions to a solution of a glycosaminoglycan and an alginic acid salt, e.g., calcium ions added to a solution of chondroitin sulfate-4 and/or -6 and sodium alginate (wherein sodium alginate is cross linked and has pockets of chondroitin sulfate-4 and/or -6 and/or non-cross-linked sodium alginate).

Of course, a Biodritin polymer network containing at least one Biodritin heteropolysaccharide can be obtained by covalently bonding the glycosaminoglycan and alginic acid salt present in a Biodritin polymer network, e.g., subjecting a Biodritin polymer network to a coupling reaction involving a linker molecule; for instance, forming network by addition of inorganic ions to a solution of a glycosaminoglycan and an alginic acid salt, e.g., calcium ions added to a solution of chondroitin sulfate-4 and/or -6 and sodium alginate, and subjecting network to coupling reaction, e.g., subjecting network to coupling reaction involving divinyl sulfone.

In preparing a Biodritin heteropolysaccharide or Biodritin polymer network comprising a Biodritin heteropolysaccharide, a solution of GAG, e.g., chondroitin sulfate-4 and/or -6 is linked to alginate, e.g., sodium alginate by covalent bonding via reaction with a linker molecule such as divinyl sulfone; the reaction is preferably in alkaline medium. In practicing the invention, one can employ a process to protect the calcium binding sites of alginate, also known as "egg-box" sites, such that no reaction occurs to these sites during the linking reaction with the linker molecule, e.g., divinyl sulfone, and GAG, e.g., chondroitin sulfate. One can also employ a process to eliminate remaining active vinyl groups in Biodritin, after linking, by reaction with an alkanolamine such as ethanolamine, preferably at alkaline pH. And, one can employ a process to purify Biodritin after the synthesis reaction which involves removal of calcium with molecule which binds to or conjugates with calcium, e.g., EDTA, preferably followed by precipitation(s) with an alcohol such as ethanol.

The invention also relates to an additional process to prepare a Biodritin polymer network comprising perfluorinated substances and dehydrothermal cross-linking of a mixture of the polymers that form a Biodritin heteropolysaccharide. The dehydrothermal reaction can be of a dry cake-containing GAG, e.g., chondroitin sulfate and alginate, e.g., sodium alginate. The cake can be produced by freeze-drying a solution containing chondroitin sulfate and sodium alginate in proper concentrations. The calcium binding sites of alginate can be protected prior to the dehydrothermal treatment by adding calcium ions to bind to the "egg-box" sites of alginate. The calcium can be removed from the "egg-box" complexes by treatment of the dehydrothermal reaction product with a material which complexes or conjugates or binds with calcium, e.g., sodium EDTA. Purification can be as discussed above.

For ease of reference, Biodritin polymer networks and Biodritin heteropolysaccharides may be termed "Biodritin" or "Biodritin products" (See also U.S. application Ser. No. 08/877,682, now U.S. Pat. No. 6,281,341 filed Jun. 17, 1997 and WO98/49202).

A primary use of Biodritin products with the perfluorinated substances and/or products derived therefrom is in applications where biocompatibility with host tissues and/or immunoisolation are issues, for example, in cell encapsulation, such as immunoisolation by microencapsulation of islets of Langerhans for diabetes control, or of other cells types or tissues. A Biodritin gel formed from Biodritin heteropolysaccharide or comprised of a Biodritin polymer network (e.g., a gel comprising at least one glycosaminoglycan, e.g., chondroitin-4 and/or -6 and at least one alginic acid salt wherein at least one of the glycosaminoglycan and alginic acid salt are cross-linked and the glycosaminoglycan and alginic acid salt are optionally (and preferably) covalently bound, preferably via a reaction involving a linker molecule such as divinyl sulfone, and the cross-linking can be performed after the covalent binding or prior thereto; generally, a Biodritin product or a product from reaction with Biodritin) can be used to form beads or microcapsules containing cells or tissues for implantation. And thus, the invention relates to such beads or microcapsules, and methods for making and using such beads or microcapsules.

Biodritin products and/or products therefrom can also be "painted", sprayed or applied to or on top of wounds, e.g., surgical wounds or sutures, and can be used to coat surgical, monitoring, or other equipment to avoid local reaction, injury or irritation. The skilled artisan can apply such without undue experimentation considering the disclosure herein and the knowledge in the art, and typical factors such as the age, sex, weight, condition of the patient, etc. or the nature of the equipment to be coated. Biodritin products and/or products therefrom serves as a matrix material for supporting cells for culturing or other applications in which cells must maintain a suspended or non-aggregated state. Accordingly, the invention relates to "paints", sprays, and matrices comprising Biodritin products and/or products therefrom, and to methods for making and using them.

The novel heteropolysaccharide and products therefrom, as well as the semi-interpenetrating polymer network, i.e., Biodritin heteropolysaccharide and products therefrom and the Biodritin polymer network, make use of: the biocompatibility of glycosaminoglycans (GAGs), preferably of a specific group of glycosaminoglycans, namely those which do not have defined cell binding properties, preferably chondroitin sulfates-4 and/or -6, herein referred to as CIS; and the desirable properties of algal polysaccharides and/or alginic acid, preferably in the form of a salt of alginic acid, e.g. M+ alginate–, wherein M is a cation, such as a metal cation, which serves as a stoichiometric counterion to balance negative charges of the alginate anion, e.g., a Group I metal, such as sodium, lithium, or other cations, e.g., organic and complex cations, e.g., ammonium. Preferably, the counterion is sodium and the salt of alginic acid is sodium alginate, which is able to form infinite gel networks in the presence of calcium ions.

The invention especially relates to an inclusion of perfluorocompounds in the polymer formulation, as emulsions produced by sonication (or other methods) as claimed and disclosed in the examples to ensure cell survival during cell or tissue encapsulation or immunoisolation for therapeutic uses.

Perfluorinated hydrocarbon derivatives are extremely dense, chemically inert, and water insoluble compounds that were developed in the early 1940's as a part of the Manhattan Project (See references 22 and 23). Researched extensively in regards to their chemical properties for years (See references 24 to 37) they were selected in the 1980's, because of their chemical inertness and their inability to be metabolized, for use as artificial blood compounds. Given their high density and their complete insolubility in water based solutions, the only means for using these compounds as an artificial blood was to generate stable emulsions using hydrophobic phospholipids and standardizing the perfluorocarbon droplet size between 0.2–0.3 µm. The research into these emulsions exploded with incomparable progress and in 1989, Flusol DA®, was the first such emulsion approved by the FDA for clinical applications for use in Percutaneous Transluminary Angioplasty. Soon, other corporate products followed, such as Oxygent® from Alliance Pharmaceuticals. The first generation emulsions, although beneficial, also had some undesirable hemodilution effects. Through the vast academic and corporate research performed with the perfluorocarbons, it was found that higher weight/volume concentrations in PFC emulsions reduced the incidence of undesired effects and improved oxygen delivery and retention properties. This second generation of emulsions had a far greater impact. In the process, the critical properties of perfluorinated hydrocarbons and derivatives were carefully documented with an amazing lack of disparity from one research group to the next.

The oxygen carrying abilities of perfluorinated compounds stem from and are directly proportional to the amount of fluorine atoms within their structure. Similarly, the oxygen content of a given emulsion is directly proportional to the environmental $pO_2$ of the emulsion and the weight percentage of the PFC in the overall volume of the emulsion. Moreover, perfluorocarbons have a kinetics of oxygen uptake and off-load that is twice as fast as the body's normal oxygen delivery system, hemoglobin. These properties are further enhanced by the delivery of high concentrations of oxygen to patients receiving PFC emulsions.

In a study of patients receiving PFC emulsions IV, beneficial increases in $pO_2$ were seen with every possible combination of gas and emulsion. With a low weight percentage emulsion (20% w/v) and room air, patients had a mean increase in $pO_2$ from 82 mm Hg to 101 mm Hg. When inspiring pure oxygen, the values went from 291 mm Hg to 361 mm Hg (32). By the same token, marked increases in tissue $pO_2$ were observed in animals following the administration of PFC emulsions. The most interesting aspect of these increases is that they persisted for several days and even when the levels of blood PFC concentrations could have been nearing zero.

Besides the studies of PFC emulsions for intravenous use as artificial blood, numerous groups have used the compounds in studies concerning reperfusion injury in harvested organs resulting from hypoxia and the preservation of physiological tissue oxygenation during transplant surgery (38–49). Summarily, the findings of these groups is that fluorocarbon emulsions or compounds have tremendous preservation effects on harvested tissue. Three such studies of particular interest are those of Kuroda et al. regarding the two layer method of pancreas preservation (50), Tanioka et al. regarding the use of the two layer method to improve islet isolation after long ischemic times (51), and the group of Urushihara et al. regarding the use of PFC's and PFC emulsions in the cold preservation of rat pancreata (52). In the first study, dog pancreata were harvested and used. This study clearly demonstrated that a simple bilayer of perfluorocarbon, which being so dense and insoluble it coalesces at the bottom of a container, with another preservation medium significantly improves the function of cold-preserved panreata, to the point of comparable graft success with pancreata immediately transplanted after harvesting.

Urushihara et al also found similarly regarding preservation by using rat pancreata. In this study, however, the design was to compare the already proven preservation capabilities of PFC's vs. PFC emulsions. In Urushihara, experimental design contained four groups. The first group consisted of pancreata perfused with a FC emulsion and then immersed in the emulsion while gassed with $95\%O_2/5\%CO_2$ mixture. The second group differs from the first group only in that 100% $N_2$ was used for gas bubbling. The third group was composed of pancreata perfused with liquid PFC, further immersed in PFC and then gassed, again with $95\%O_2/5\%CO_2$. The fourth and final group is the same as the third group with the exception of using 100% $N_2$ as the bubbling gas. The function of the organs after culture time was then assessed by graft transplantation (syngeneic) under the following criteria for a successful graft: if the graft reduced STZ induced hyperglycemia to levels below 200 mg/dL within 24 hours, and if this level was maintained for greater than two weeks, then a graft was deemed functional. Urushihara found that there was preservation in all groups for 24 hours, but at 48 hours all but group 3 had 0% graft success. Group 3, liquid PFC with $95\%O_2/5\%CO_2$, was markedly superior to all the other groups in every aspect of preservation. Of the organs in the 24-hour culture group, 100% of the grafts transplanted were functional. Of the 48 hour culture group, 80% of the grafts transplanted (⅘) were functional. When compared to the 12–16 hour preservation times afforded by the standard organ procurement solutions, such as UW solution, PFC shows a distinct advantage. In fact, a group at the University of Washington is now using a two layer PFC method for perfusing pancreata after harvest and have seen substantial improvements in preservation time.

Of particular importance to our field of study, the group of Tanioka et al. applied the two-layer method to pancreatic islet cell harvesting. Their study was divided into five groups: The first group of dog pancreata were harvested and preserved for three hours using a bilayer of UW solution and PFC. At the end of this period, the Islets of Langerhans were isolated from the pancreata using the Ricordi method of human islet isolation modified for rat pancreata (53). The second group employed the same preservation method as the first, but for a period of 24 hours, at which time the islets were isolated. The third and fourth groups used just UW solution as a preservation media. In all of the first four groups, $95\%O_2/5\%CO_2$ was bubbled in the preservation containers. The final group was an immediate harvest and autologous transplant group, as a control.

After the preservation periods and islet isolations in Tanioka, the islets were counted (pre-purification on a Ficoll gradient and post-purification), and transplanted, through cannulation of a mesenteric vein, into the liver. As in previous whole pancreas studies, graft success was determined by the reversal of hyperglycemia (glucose values below 200 mg/dL) in the pancreatectomized autologous donors, and by the maintenance of this reversal for a significant period of time. In the control group, the percentage recovery of the islets (post-purification count/pre-purification count) was 65.4% with 5000 IEQ's/g of pancreas recovered. The experimental groups at three hours had values of 63.3% for the bilayer PFC group (5600 IEQ's/g of pancreas) and 59.3% for the UW group (4700 IEQ's/g of pancreas). Values at 24 hours of cold preservation for the two groups were 56.4% for the bi-layer PFC group (4000 IEQ's/g of pancreas) and 39.3% for the UW group (1300 IEQ's/g of pancreas). In the cell counts alone, the advantage of the use of PFC's in the preservation prior to isolation was apparent. Further evidence for the superiority of the two-layer method in organ, and even single cell preservation, were the graft success rates. The control group had a graft success rate of 89% (⅘) transplants. The three hour experimental groups had rates of 83% (⅚, bi-layer PFC group) and 33% (⅔, UW group). The experimental 24 hour groups had rates of 56% (⅗, bi-layer PFC group) and 0% (%, UW group). This overwhelming evidence suggests that not only do perfluorocompounds act as a beneficial preservation media in whole organ harvesting, but also can be used in the preservation of isolated cells, such as the islets of Langerhans.

The arguments for the use of perfluroemulsions and perfluorocompounds in the area of cell and tissue preservation are sound. These findings established the background for our invention that is now described.

Therefore, the invention, even more broadly, relates to:

A composition comprising at least one glycosaminoglycan, at least one alginate and at least one perfluorocarbon substance, e.g., at least one emulsified perfluorocarbon substance to increase oxygen availability for encapsulated and/or immunoisolated cells and tissues, wherein:
  the at least one glycosaminoglycan and/or the alginate are cross-linked or polymerized, e.g., the alginate is cross-linked or polymerized, for instance by addition of an inorganic salt, such as a calcium salt; or
  the at least one glycosaminoglycan and the alginate are covalently bound, e.g., by means of a coupling reaction involving a linker molecule such as DVS; or
  the at least one glycosaminoglycan and/or the alginate are cross-linked or polymerized, e.g., the alginate is cross-linked or polymerized, for instance by addition of an inorganic salt, such as a calcium salt, and the at least one glycosaminoglycan and the alginate are covalently bound, e.g., by means of a coupling reaction involving a linker molecule such as DVS, and the covalent binding can have been performed prior to cross-linking or polymerizing or vice versa;

Adding to or using with Biodritin an emulsified perfluorocarbon substance to increase oxygen availability to encapsulated and/or immunoisolated cells and tissues;

Gels comprising the composition; mixtures of such gels or of at least one such gel and at least one such composition;

Methods for making such compositions and gels;

Methods for using such compositions and gels, including as "paints", sprays, matrices, beads, microcapsules;

Products comprising the composition or gel, e.g., "paints", sprays, matrices, beads, microcapsules; and The perfluorocarbon substances including but not limited to perfluorotributylamine (FC-43), perfluorodecalin, perfluorooctyl bromide or bis-perfluorobutyl-ethene.

A Biodritin heteropolysaccharide solution is transformed into gel microcapsules by dripping the solution into a calcium chloride solution. A Biodritin heteropolysaccharide solution is fashioned into a slab of any desired shape by contacting the Biodritin heteropolysaccharide and calcium chloride solution and thus gelling the Biodritin in the forms of the desired shape, such that the shape of the gel may be varied, as desired. The gel microcapsules or slab can have pancreas islets of Langerhans therein.

Biodritin can also be formed into a "spaghetti"-like structure, prepared by extrusion of a Biodritin heteropolysaccharide solution over a line, e.g., through a cylindrical catheter tube containing inside a cotton or surgical line. The Biodritin solution is extruded together with the line into a calcium ion containing solution, whereby a gel instantly forms that contains the line. The gel is then matured in a calcium ion solution. One can form a protective outer layer, e.g., of poly-lysine/Biodritin, over the Biodritin spaghetti, to provide limited permeability to the device. The structuring of the spaghetti device is by the line in the interior and extending further out therefrom towards the surrounding gel cylinder, e.g., by the lateral extensions of the line, or by those provoked on the surface of the line by scraping it, e.g., with a knife blade.

A Biodritin spaghetti string can be used for implantation of cells or tissues therein contained, e.g., from the lateral extensions; or more than one Biodritin spaghetti strings may be used by being tied up together at each end. The strings can be further inserted within a biocompatible material such that the Biodritin spaghetti strings are protected from mechanical strains after implantation. And, these string devices can be used as a means of implanting cells or tissues in humans and animals for disease prevention or treatment, as is the case of islets of Langerhans implants for diabetes treatment.

The skilled artisan can implant a composition containing cells, such as islet cells, without undue experimentation, taking into account typical factors such as the age, sex, condition etc. of the patient, and the rate of secretion of a desired expression product of the cells, e.g., insulin (see also U.S. Ser. No. 08/417,652, filed Apr. 5, 1995, now U.S. Pat. No. 5,808,050 issued Sep. 15, 1998 incorporated herein by reference).

Thus, the invention relates to these products and methods for preparing and using them for encapsulating cells and tissues in a long term culture, transportation and/or transplantation in a medical treatment.

Analogous methods can be used to prepare products from Biodritin polymer networks; and, the invention accordingly relates to these products and methods for preparing and using them.

With respect to glycosaminoglycans, such as heparin sulfate, heparin and hyaluronic acid, these are not preferred for the invention as they can have defined cell-binding properties. With respect to material having defined cell binding properties which renders them unsuitable for use in the instant invention, hyaluronic acid binds specifically to CD-44, also known as "lymphocyte homing receptor" (Hermes-antigen) or "major hyaluronic acid receptor of mammalian cells" (Aruffo et al, 1990). CD-44 is expressed on the surfaces of most mammalian cells, rodent and primate hematopoietic cell types, fibroblastoid, neural and muscle cells (Rosenmann and St. John, 1993). Hyaluronic acid also binds to Versican, a large proteoglycan secreted by fibroblasts that promotes cell adhesion through interactions with components of the extracellular matrix and cell surface glycoproteins (Zimmermann, 1993).

Further, as to the use of materials having undesirable defined cell binding properties, heparin is also not preferred to be linked to alginate in the composition due to its well-known inhibition of the blood clotting mechanism. Heparan sulfate is also not preferred on the basis of its participation in cell-cell adhesion mechanisms. Heparan sulfate is linked to a membrane-bound proteoglycan that binds NCAM (neural cell adhesion molecule), thereby promoting homophilic cell adhesion (Cole et al, 1986). The Heparan sulfate binding domain of fibronectin is responsible for the binding of neurons, lymphocytes and other cell types to fibronectin, in the process of cell-cell adhesion (Liao et al, 1988). Further, heparan sulfate proteoglycans found on cell surfaces and in the extracellular matrix are binding sites for the basic fibroblast growth factor (bFGF) (Moscatelli et al, 1988).

Thus, having established that CIS is the most desirable glycosaminoglycan to utilize for the purposes of the present invention, the inventive heteropolysaccharides arise from stable, covalent chemical bonds between the structures of the at least one alginic acid salt, e.g., sodium alginate and the at least one glycosaminoglycan, e.g., CIS, for example, by a coupling reaction with divinyl sulfone, DVS. These reactants can produce a novel neo-hetero-polysaccharide conjugate having desired properties for use in cell and tissue biology, whenever biocompatibility and/or immunoisolation are critical issues. Along the same line, a semi-interpenetrating polymer network can be prepared by mixing CIS and alginate, at desired concentrations and forming a gel by addition of calcium ions that has similar properties to and benefits of the inventive heteropolysaccharides.

Thus, the invention can relate at least to two processes.

First, the present invention provides a process for preparing a heteropolysaccharide comprising covalently bonding at least one glycosaminoglycan, e.g., CIS, and at least one alginic acid salt, e.g., sodium alginate, preferably by a coupling reaction with a linker molecule, e.g., DVS, and an emulsified perfluorocarbon substance, including but not limited to perfluorotributylamine (FC-43), perfluorodecalin, perfluorooctyl bromide or bis-perfluorobutyl-ethene, such that the calcium binding sites in alginate are preserved and/or conserved during the coupling reaction. These sites provide the flexibility of using the heteropolysaccharide as a sol or a gel of desired strength, or as a composition having adjustable viscosity; and, the present invention relates such products from the heteropolysaccharide and to method for making and using them, e.g., by contacting with ions, such as calcium ions to prepare a gel, for instance, an infinite gel.

The second process forms a physical gel, e.g., of the semi-interpenetrating polymer network type, by addition of a polymerizing or cross-linking agent, e.g., calcium ions to a solution containing both at least one alginate, at least one glycosaminoglycan, e.g., chondroitin sulfate-4 and/or -6, and an emulsified perfluorocarbon substance, including but not limited to perfluorotributylamine (FC-43), perfluorodecalin, perfluorooctyl bromide or bis-perfluorobutyl-ethene. This gel can be a composition that can be varied to suit specific applications. The inventive s-IPN gel is stable and is formed by the complexation of calcium ions with poly-guluronic blocks of alginate to form the "egg-box" structures that stabilize the gel.

Still, further within the principles just delineated, another formulation can be prepared by suitable combination of the formulations described above, in which a given amount of the covalently bound heteropolysaccharide conjugate is mixed in solution with alginate and CIS, to which solution calcium ions are added to form the gel.

Likewise, another formulation can be prepared by subjecting an inventive gel to a linking reaction so as to covalently bond glycosaminoglycan and alginate units to each other, e.g., by subjecting the gel to a coupling reaction involving a linker molecule such as DVS.

The invention further relates to uses of gels and compositions which can be formed into gels, especially biocompatible gels, such as in "paints", sprays, matrices, beads, microcapsules, and the like, including novel uses such as "spaghetti"-like material comprising a spine, e.g., a suture or thread, having a desired material connected thereto, e.g., cells connected to the spine, and an inventive gel surrounding the spine, e.g., in a cylindrical manner.

Documents are cited in this disclosure with a full citation for each appearing thereat and/or in a Reference List. These documents relate to the state-of-the-art to which this invention pertains, and each document cited herein and each document referenced or cited in a herein-cited documents are hereby incorporated by reference.

BACKGROUND OF THE INVENTION

Cells and tissues may be immobilized and immunoisolated by three basic techniques: in extravascular chambers isolated but in the path of the blood stream, in spherical dispersions or microcapsules, and within macrocapsules. Using these techniques a great variety of cells and tissues of different animals have been immunoisolated and implanted in animals for development of therapeutic systems (reviewed by Christenson et al (1993)). Indeed, future applications of immunoisolated cell therapy are envisaged for diseases or conditions such as diabetes, hemophilia, hepatic failure, Alzheimer's, Parkinson's and Huntington's diseases, affective disorders, hepatic failure and fertility problems (Christenson et al, 1993). A complete review of the questions involved in encapsulation and immunoisolation is presented in a recent volume edited by Goosen (1993).

In the case of diabetes mellitus, alternatives to daily insulin injections have been searched for control of type I diabetes, or insulin-dependent diabetes mellitus (IDDM). These included pancreas transplants, pumps to deliver insulin under a controlled program and, more recently, Langerhans' islets transplantation. A review of sustained-release implants for insulin delivery has been published (Wang, 1991).

Several researchers have proposed different approaches to protect islet tissue from host attack after transplantation; these include encapsulation of islets in different materials such that insulin may be secreted but the beta cells in the islet tissue will be immunologically isolated from the host. Polysaccharides have been proposed to form membranes, as is the case of agarose, by Howell et al (1982) or alginate, by Tze and Tai (1982). Materials used include synthetic polyacids and poly-bases, gelatin and polyamino acids (Young et al, 1989) as well as different polysaccharides: chemically modified dextran, to form poly-ionically bonded capsules (Lim and Hall, 1988, PCT Int. Appl. WO 8,800,327), entrapment in alginate followed by stabilization with poly-lysine and alginate (Chang and Wong, 1992, U.S. Pat. No. 5,084,350), as well as a combination of chitosan and carboxy-methyl cellulose to form capsules of controlled permeability (Shioya and Hirano, 1990, U.S. Pat. No. 5,089, 272).

Additionally, recent work bearing on regeneration of skin in culture has pointed out the important role of GAG's in the process, in studies where mixtures of collagen and GAG were used as support (Murphy et al, 1990; Yannas et al, 1990). Along the same line, keratinocytes and fibroblasts grown on a nylon mesh produced a dermal-like matrix containing proteoglycans (Slovakia et al, 1993).

The importance of the extra-cellular matrix components for the normal development of the skin system lends support to a basis of the instant invention, e.g., that foreign molecules combined or structured with specified GAG's, e.g., preferably CIS in the case of this invention, will constitute ideal protecting materials in transplantation or implantation of cells or tissues of human or animal origin, with the purpose of treating or controlling disease.

However, the art heretofore fails to teach or suggest the particular heteropolysaccharides polymer networks containing additionally an emulsified perfluorocarbon substance which is capable of increasing oxygen availability for encapsulated and/or immunoisolated cells and tissues, thus, prolonging the vitality of the encapsulated cells and tissues for transportation and/or transplantation, and products therefrom and processes and uses of the invention.

Further, essential constituents of the extra-cellular matrix in connective tissues, of cell membranes and endothelial lining, and the overall presence of GAG's demonstrates their importance in matrix formation and extension, and in cell-matrix and cell-cell interactions. Although GAG's occur in an organism mostly linked to proteins, as proteoglycans, it has been demonstrated that only the protein portion is immunogenic; the glycosaminoglycan, e.g., CIS component, is not immunogenic by itself (Hirschmann and Dziewiatkowski, 1966; Loewi and Muir, 1965).

However, use of a GAG with an alginate salt, for instance GAG-alginate biomolecules, e.g., via a coupling reaction with a linker molecule, to form a heteropolysaccharide conjugate and products therefrom and processes and uses of the invention are not heretofore taught or suggested. Moreover, the formation of a polymer network, e.g., of a semi-interpenetrating polymer network, based on the two components, alginate and GAG, e.g., CIS, rendered in gel form by addition of ions such as inorganic ions, e.g., calcium ions, has not been taught nor suggested in the prior art. Nor has a polymer network comprising a heteropolysaccharide from coupling GAG-alginate present in a GAG-alginate polymer network, been heretofore taught or suggested.

In the case of diabetes, the depth of interest in discovering the best way to use islets in transplantation is demonstrated by two recently published papers, one dealing with storage and preservation of islets (Jindal and Gray, 1994) and the other with the action of prednisone on the islet autograft function (Rodrigues Rilo et al, 1994).

U.S. Pat. No. 4,409,331 to Lim relates to the encapsulation of islets in polymeric material formed from alginate and poly-lysine; Lim and Sun (1980) discussed the microencapsulation of islets to form a bioartificial pancreas. Chitosan microspheres were developed that bind to GAG receptors on cell surfaces (Gallo et al U.S. Pat. No. 5,129,877). Collagen-GAG microcapsules were proposed as drug delivery systems, to deliver anti-microbial agents (Rase et al U.S. Pat. No. 5,169,631). Polyacrylates were also developed as encapsulation materials and have also been co-polymerized with alginate, as discussed by Stevenson and Sefton (1993). However, use of GAG having an emulsified perfluorocarbon substance with an alginate salt, GAG-alginate biomolecules, e.g., in physical mixture or bound via a coupling reaction with a linker molecule, to form a heteropolysaccharide or a physical network, e.g., s-IPN, gel and products therefrom and processes and uses of the invention, are not taught or suggested.

It is emphasized, however, that none of the art heretofore has GAG containing a perfluorinated substance acted as the major biocompatibility agent between a foreign chemical structure or device and host organism, especially in a composition with an alginate.

The synthesis and properties of glycoconjugates has been reviewed in a book edited by Lee and Lee (1994). The new class of structures now being described herein belongs to a group of glycopolymers formed by joining together two different natural heteropolysaccharides by reaction with an unnatural tether e.g., divinyl sulfone. This new class would enter the list of neoglycoconjugates compiled by Magnusson et al (1994) under the heading "glycopolymers with gel forming properties".

On the other hand, the physical gel formed by adding calcium ions to solutions containing variable concentrations of GAG, e.g., CIS, and alginate belongs to the group of polymers known as semi-interpenetrating polymer networks, recently discussed by LaPorte (1997). In this category, one type of polymer is enmeshed and entrapped by a second polymer, which is cross-linked to stabilize the structure.

However, that compositions of the invention may be characterized as "glycopolymers with gel forming properties" or as a "polymer network", e.g., "a semi-interpenetrating polymer network" does not mean that the invention has heretofore been taught or suggested.

SUMMARY AND OBJECT OF THE INVENTION

Thus, the present invention provides a novel hetero-polysaccharide conjugate or complex, gels and/or sols derived therefrom, and to the synthesis, purification and utilization of a novel glycopolymer and/or heteropolysaccharide and/or gels with a perfluorinated substance, solutions and/or sols, herein referred to as Biodritin composition. The inventive hetero-polysaccharide is preferably formed from covalent bonding between at least one glycosaminoglycan, e.g., chondroitin sulfate-4 and/or -6, and at least one alginic acid salt, e.g., such that a gel and/or sol is formed, e.g., and a perfluorinated substance such as an emulsified perfluorocarbon substance preferably but not limited to perfluorotributylamine (FC-43), perfluorodecalin, perfluorooctyl bromide or bis-perfluorobutyl-ethene, in the presence of an appropriate counterion, e.g., calcium.

An additional formulation of the invention combines the two polysaccharides, alginate and GAG, e.g., CIS, in aqueous solutions having variable concentrations of either component, through the formation of a gel of the type semi-interpenetrating polymer network, by addition of a cross-linking or polymerizing agent, e.g., calcium ions. A third formulation combines the two concepts in the same preparation, in suitable proportion, which can be established by the skilled artisan, without undue experimentation, from this disclosure and the knowledge in the art.

Therefore, the invention, provides:

a composition comprising at least one glycosaminoglycan, e.g., CIS, an emulsified perfluorocarbon substance, and at least one alginate, e.g., sodium alginate, wherein:

the at least one glycosaminoglycan and/or the alginate are cross-linked or polymerized, e.g., the alginate is cross-linked or polymerized, for instance by addition of an inorganic salt, such as a calcium salt; or the at least one glycosaminoglycan and the alginate are covalently bound, e.g., by means of a coupling reaction involving a linker molecule such as DVS; or the at least one glycosaminoglycan and/or the alginate are cross-linked or polymerized, e.g., the alginate is cross-linked or polymerized, for instance by addition of an inorganic salt, such as a calcium salt, and the at least one glycosaminoglycan and the alginate are covalently bound, e.g., by means of a coupling reaction involving a linker molecule such as DVS, and the covalent binding can have been performed prior to cross-linking or polymerizing or vice versa; and, having a perfluorinated substance in the Biodritin polymer formulation, the perfluorinated substance is preferably an emulsified perfluorocarbon substance, preferably but not limited to perfluorotributylamine (FC-43), perfluorodecalin, perfluorooctyl bromide or bis-perfluorobutyl-ethene, gels comprising the composition; mixtures of such gels or of at least one such gel and at least one such composition; and, methods for making such compositions and gels; and methods for using such compositions and gels, including as "paints", sprays, matrices, beads, microcapsules; and, products comprising the composition or gel, e.g., "paints", sprays, matrices, beads, and microcapsules.

The inventive composition can be obtained by admixing 0.5% to 5.0%, e.g., 1% to 3%, by weight or by volume of alginate, e.g., sodium alginate, and about 1.0%, e.g., 1.5% or 2.0%, to up to 20% to 30%, e.g., 25%, by weight or by volume of GAG, e.g., CIS. That is, in general, in forming inventive compositions the alginate to GAG ratio can be 0.5:30; but, preferably three (3) to four (4) times more GAG is present than alginate (by weight or by volume), i.e., a preferred alginate to GAG ratio in forming inventive compositions is 1:3 to 1:4. Alginates come in varying viscosities, e.g., high viscosity, medium viscosity. Medium viscosity alginates are preferred as high viscosity alginates can result in harder beads. Further, the amount of alginate employed in forming an inventive composition can be limited by the viscosity of the alginate; with a medium viscosity alginate, 5% by weight or volume alginate is rather viscous. Furthermore, the skilled artisan can readily appreciate that the volume and viscosity or hardness of compositions, gels and products therefrom, e.g., beads, etc. can be varied without undue experimentation by varying the amount of GAG, e.g., CIS and alginate, e.g., sodium alginate. For instance, when a softer composition, gel or product, having more volume, is desired, more GAG is employed, i.e., the amount of GAG by weight or volume is increased; and, when physical resistance, hardness, and like properties are desired, more alginate is employed, i.e., the amount of alginate by weight or volume is increased.

When a linker molecule is used in forming an inventive compound, it can be used in an amount relative to the amount of alginate, or to the amount of GAG present, e.g., an amount from 50% of to equal by weight, volume or stoichiometrically to the amount of alginate present, or to the amount of GAG present, or twice or thrice the weight, volume or stoichiometric amount of alginate or GAG present. When an inorganic ion is used as a cross-linking or polymerizing agent in forming a composition of the invention, the inorganic ion is preferably a calcium ion, e.g., calcium chloride, which can be used in an amount relative to the amount of alginate present, e.g., in an amount of about 0.05% to 2.0% by weight or by volume, e.g., about 1.0% by weight or by volume.

Gels can be essentially covalent, or part covalent and part interpenetrating. From analysis of inventive gels, e.g., HPLC analysis showing bands corresponding to alginate, CIS and a covalent structure, it is believed that gels of the invention form interpenetrating networks. However, Applicants do not necessarily wish to be bound by any one particular theory.

Biodritin containing an emulsified perfluorocarbon substance can be applied to surgical wounds or sutures, to protect from adherences; it also serves as a matrix material for supporting cells for culturing or other applications, particularly, in which cells must be maintained with high vitality and suspended in a non-aggregated state.

An object of the invention is to provide a composition capable of supporting cells for culturing, transportation and/or transplantation wherein the cells can be maintained in vitro long term and with high vitality and low mortality rate by having a composition capable of enhancing oxygen diffusion.

In this disclosure, "comprises", "comprising" and the like can have the meaning ascribed to them in U.S. Patent Law and can mean "includes", "including" and the like.

These and other embodiments will be described and/or will be obvious from the following detailed description.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 shows a histological pattern of islets encapsulated in slabs 3×10×20 mm, cultured in vitro. Forty thousand human islets equivalents (IEQ), were encapsulated in each slab and cultured for 14 days at 37° C. in CMRL medium with 10% fetal calf serum. Controls had no FC-43; experimental had 10% v/v FC-43.

DESCRIPTION OF THE INVENTION

Figure 1:
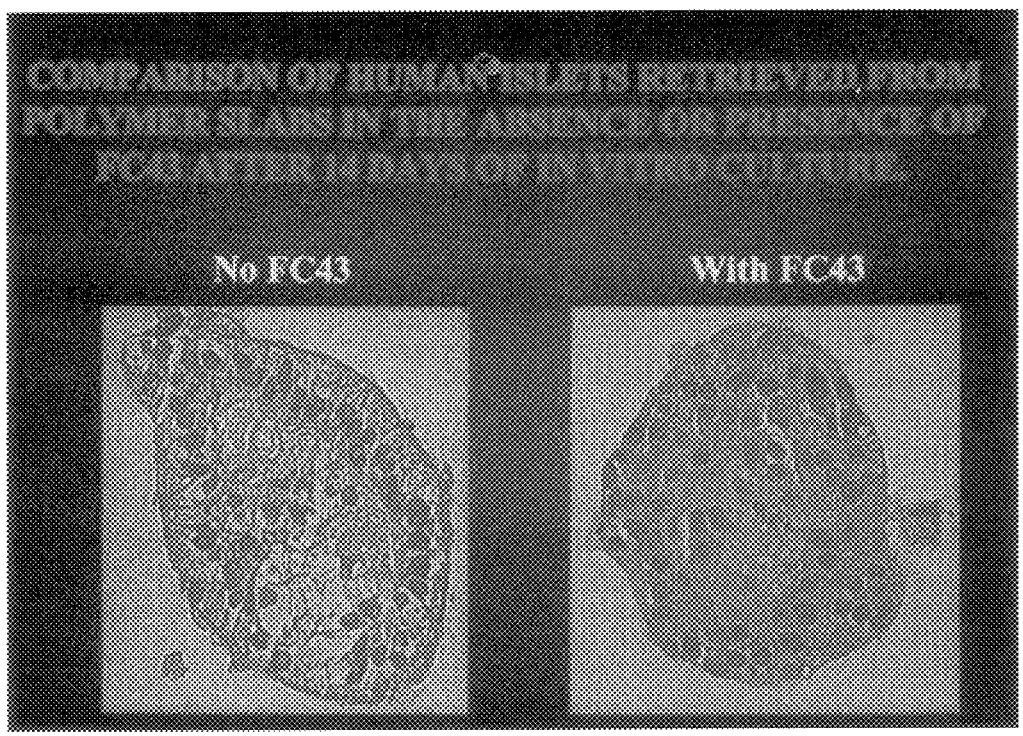
FIG. 1 shows a comparison of human islets retrieved from polymer slabs in the absence or presence of FC43 after fourteen days of in vitro culture. Specifically.

Without wishing to necessarily limit the foregoing, the following shall discuss the invention with respect to certain preferred embodiments. It has now been found that the chemical polymerization of an algal polysaccharide, alginic acid, under the form of sodium alginate, with a specific group of animal heteropolysaccharides, e.g., chondroitin sulfate-4 and -6, CIS, results in new materials, e.g., Biodritin, that can be classified as neo-heteropolysaccharide conjugates having novel properties in relation to the parent molecules, while preserving most of the chemical characteristics of both parent molecules. The general properties of this new class of compounds include any or all, and preferably all of Biodritins are polyanions, carrying both carboxylate and sulfate groups (alginate contains carboxylates, while chondroitin sulfate contains both carboxylates and sulfates); Biodritins form infinite gels when treated with calcium ion, a property imparted by the alginate moiety. Biodritins dissolve readily in water. Additionally, the viscosity of the solutions can be regulated by adjusting the concentration of Biodritin, as well as the concentration of calcium.

Biodritins can also be prepared by polymerization of CIS and alginate, in mixed solutions, by addition of calcium ions, thereby resulting in the formation of stable gels of semi-interpenetrating polymer network, in which the CIS component is entrapped in the gel network formed by calcium alginate.

By adding calcium in sufficient concentration, Biodritins form stable gels, as the synthesis process of the invention was designed to preserve, with extreme care, the calcium binding sites in the alginate component. The presence of the chondroitin sulfate component, on the other hand, imparts a stronger negative charge of sulfates and similarity to an extra-cellular matrix to Biodritins, rendering them entirely biocompatible for applications in transplantation of cells and tissues, among others.

Biodritin-derived materials can have their permeability barrier controlled by ionic complexation with positively charged polymers such as poly-L-lysine or poly-L ornitine, which form a thin external capsule to the gel. The pore size of this capsule can be adjusted as desired, by changing the concentration and molecular weight of the positively charged polymer during capsule formation.

In the synthesis of the invention compositions, Biodritin preferably has a GAG content ranging from 2 to 200% of the alginate composition by weight, depending on the specific reaction conditions. The final composition can be adjusted by combining Biodritin that has been cross-linked with Biodritin formed by the gelling of alginate and CIS and an emulsified perfluorocarbon substance, in the same solution. Within this range, the compounds have the desired properties for use as transplantation materials and having an emulsified perfluorocarbon substance will dramatically increase the supply of oxygen to cells and tissues encapsulated within the composition of the present invention, thus prolonging the longevity and vitality of the encapsulated cells and/or tissues for transportation and/or transplantation. Insoluble materials can also be prepared by controlling the polymerization conditions. These may have utility as fillers in tissue repair, or as surfaces to allow cell growth in culture.

The surface of Biodritin beads exposed to an aqueous solvent carries the functionalities of both alginate and chondroitin sulfate (GAG) carboxylates, sulfates, hydroxyls, as well as glycosidic links and the sulfone group of the cross-linker moiety; the negatively charged sulfate and carboxylate groups are able to form strong ion-ion complexes with polycations such as poly-lysine or poly-ornithine, thereby providing additional external structure and protection to the beads, which has been observed for alginate capsules. These complexes formed at the outer surface of the microcapsules also help to define pore sizes.

The viscous solutions obtained by dissolving Biodritin in water or saline or other desired aqueous medium are easily handled, especially if the concentration is kept under 4% (w/v) and that they are not exposed to calcium ions. Such solutions can be transformed into infinite gels by complexation with calcium ions; e.g., by dripping them from syringes or capillaries into solutions of calcium chloride one obtains microbeads of desired spherical size. Further treatment with positively charges molecules such as poly-lysine results in a thin external capsule that may, again, be protected by layering Biodritin on top of it from a dilute solution.

A Biodritin solution can be extruded, e.g., from a thin tubing directly into a calcium chloride solution, whereby a gel in the form of a rod or cylinder of uniform diameter is obtained. Cells or tissues can be held within these cylinders for the purposes of culturing or transplantation.

The Biodritin gel may also be conformed, e.g., as a slab of desired size and shape where cells or tissues may become entrapped, for purposes of culturing or implantation.

Another use of Biodritin is in the protection of recent sutures: a Biodritin sol may be "painted" or applied directly with a sterile brush or sprayed around the suture area, followed by spraying with an appropriate calcium chloride solution. A soft, protecting gel forms immediately around the suture area, protecting it from invading cells by blocking cell adhesion. Biodritin gel itself can be sprayed, painted or applied on a suture to protect it from adherences. The skilled artisan can determine the suitable viscosity of the gel and the amount thereof to employ to spray, paint or apply, without undue experimentation, from the knowledge in the art, the disclosure herein, and typical factors such as the wound or suture, and the condition of the patient.

The chemical coupling of the two major Biodritin components, preferably, sodium alginate and chondroitin sulfate-4 and/or -6 is carried out by reaction with a linker molecule, e.g., divinyl sulfone, abbreviated DVS. A linker molecule is a small molecule that is very susceptible to nucleophilic attack (See U.S. Ser. No. 08/417,652, now U.S. Pat. No. 5,808,050, incorporated herein by reference, with respect to other types of linker molecules and types of coupling reactions). The reaction is carried out at alkaline pH, under conditions which allow the calcium binding sites in alginate to be protected from reaction. The final product of the cross-linking reaction is then rendered soluble and can be separated from the reagents through purification by repeated alcohol precipitation.

The concentration of linker molecule, e.g., DVS, used in the reaction can define the final solubility of the glycopolymer complex; beyond a certain range insoluble materials are formed.

An alternative to the chemical coupling of CIS and alginate is the preparation of Biodritin by formation of a physical gel from a solution containing both polymers, in desired concentrations. This gel forms when calcium ions are added, and the resulting gel is of the semi-interpenetrating polymer network type, s-IPN. In this type of polymeric gel, the cross-linked structure is derived from only one component, e.g. alginate, by the formation of the "egg-box" structures resulting from the binding of calcium ions to poly-guluronic blocks in alginate. The resulting gel network entraps and holds the CIS chains that are intertwined with alginate, such that CIS molecules remain as components of the gel structure, imparting to that gel structure the properties of CIS.

An element of the invention is the ability of the final product, Biodritin, to form gels with calcium ions and to provide the encapsulated cells and/or tissues with ample supply of oxygen. This is achieved by protecting the calcium binding sites in alginate, also called "egg-box" sites, from reacting with the cross-linking reagent during the synthesis of the chemically coupled variant of Biodritin. This is accomplished by adding the appropriate amount of calcium ions to the alginate solution prior to the coupling reaction in such a way that the calcium-"egg-box" complexes are pre-formed, while avoiding strong gelling, and the solution co-polymerization reaction is not blocked.

Early in the purification steps of the final product the protecting calcium ions are removed from the "egg-box" complexes, allowing for the dissolution of the particles to form a viscous solution that can, then, be treated as desired.

Perfluorinated hydrocarbon derivatives are extremely dense, chemically inert, and water insoluble compounds that were developed in the early 1940's as a part of the Manhattan Project. Researched extensively in regards to their chemical properties for years they were selected in the 1980's, because of their chemical inertness and their inability to be metabolized, for use as artificial blood compounds. Given their high density and their complete insolubility in water based solutions, the only means for using these compounds as an artificial blood was to generate stable emulsions using hydrophobic phospholipids and standardizing the perfluorocarbon droplet size between 0.2–0.3 μm. The research into these emulsions exploded with incomparable progress and in 1989, Flusol DA®, was the first such emulsion approved by the FDA for clinical applications for use in Percutaneous Transluminary Angioplasty. Soon, other corporate products followed, such as Oxygent® from Alliance Pharmaceuticals. The first generation emulsions, although beneficial, also had some undesirable hemodilution effects. Through the vast academic and corporate research performed with the perfluorocarbons, it was found that higher weight/volume concentrations in PFC emulsions reduced the incidence of undesired effects and improved oxygen delivery and retention properties. This second generation of emulsions had a far greater impact. In the process, the critical properties of perfluorinated hydrocarbons and derivatives were carefully documented with an amazing lack of disparity from one research group to the next.

The oxygen carrying abilities of perfluorinated compounds stem from and are directly proportional to the amount of fluorine atoms within their structure. Similarly, the oxygen content of a given emulsion is directly proportional to the environmental $pO_2$ of the emulsion and the weight percentage of the PFC in the overall volume of the emulsion. Moreover, perfluorocarbon have a kinetics of oxygen uptake and off-load that is twice as fast as the body's normal oxygen delivery system, hemoglobin. These properties are further enhanced by the delivery of high concentrations of oxygen to patients receiving PFC emulsions.

More specifically, given a kinetics of oxygen diffusion that matches hemoglobin at normal $pO_2$'s and exceeds hemoglobin at critically hypoxic $pO_2$'s, and given the inertness and biocompatibility of the perfluorocompounds, the potential benefits of the substances are enormous, particularly in the field of cell and tissue encapsulation and engineering.

These substances, such as perfluoro-tributylamine, are commercially available; FDA approved mixtures of perfluorocompounds, made as fine emulsions (with micelle sizes <0.2 micrometers) necessary for use in blood vessels. However, to date, no one has modified these substances to be used to enhance oxygen diffusion and availability in immunoisolation or tissue transplantation devices, the object of our invention.

Using a novel heteropolysaccharide, composed of Chondroitin A (CIS) and Sodium Alginate in varying mixture concentrations, with or without cross-linking, an applicable polymer for immunoisolation purposes has been developed (Mares-Guia and Ricordi, Pat. Appl. 1997, ref 1). Accordingly, the present invention teaches and claims a method for including perfluorohydrocarbon derivatives within the polymer matrix to improve oxygen availability and transport to encapsulated cells or tissues. The polymer is then formed into gel-like devices of any geometrical configuration using interfacial coacervation, a process by which the polymer matrix is extruded into 1.5% w/v calcium chloride solution and through ionic bonds, the positively charged calcium ions form bridges between the negatively charged carboxylate groups present in the Sodium Alginate portion of the polymer matrix. The remainder of the matrix is trapped within the gelated core of the device, including the oxygen diffusion enhancing emulsion.

The ability of the inventive compositions to easily and rapidly go from solution to gel and from gel to solution, by manipulation of the calcium ion concentration, is another significant property of the invention, as it leads to additional applications of this new material outside the transplantation field.

In another embodiment of the present invention, the chemical combination of alginate, e.g., sodium alginate and GAG, e.g., chondroitin sulfate-4 and/or -6 is made by dehydrothermal reaction, at temperatures of about 100° C. In this case, DVS is not used and ester bonds are formed between the alcoholic hydroxyls and acidic groups in alginate and chondroitin sulfate. Also using DHT, protection of the "egg-box" sites is obtained, and this is useful for preservation of the gelling properties of Biodritin.

It is emphasized that, given the purification steps after reaction, commercially available reactants have been used in all tests herein without preliminary purification, and with no negative effects on the properties of the final product, Biodritin.

The invention shall be further described by way of the following non-limiting Examples that are also an illustration of the invention, and are not to be considered a limitation of this invention, many apparent variations of which are possible without departing from the spirit or scope thereof.

EXAMPLES

Example 1

Preparation of the Reactant Solutions

Chondroitin sulfate: the commercial CIS used contains 70% of 4-sulfate and 30% of 6-sulfate; 2.5 g was allowed to dissolve in 25 ml 0.1 M sodium carbonate solution, to give a 100 mg/ml final concentration. In other formulations, higher concentrations of CIS are used, to give final concentrations of 150, 200 or 250 mg/ml.

Sodium alginate (5.0 g) was suspended in 45 ml of water, heated to 40° C., after which another 30 ml water were added in 10 ml portions to facilitate dissolution and decrease viscosity of the final solution. The amount of sodium alginate used corresponds to 28.3 mmoles of the unit disaccharide residue of alginate (F.Wt.=176.2).

The polymer used in the encapsulation according to the present invention is known as Biodritin; a mixture used to prepare the polymer solution is 70% Sodium Alginate mixed with 30% CIS, with or without chemical cross-linking (See U.S. patent application Ser. No. 08/877,682 and WO98/49202). Generally, a 20 gram powder mixture is made and purified (14 g Alginate, 6 g Chondroitin sulfate A). The mixture is twice sterilized using first a double ethanol extraction followed by drying and sterile grinding and then, a chloroform ethanol soak. It is air dried in a sterile hood and then transferred to sterile 25 mL conical tubes. The polymer solution is prepared by weighing the powder in the sterile hood, 1.25 g, to be added to 25 mL of sterile culture media and sterile perfluorocompound mixed solution. The amount added is enough to make a 4% to 9% w/v solution, found to be the soundest structural concentration range under calcium chelation tests with 50 mM sodium citrate solutions. For a 25 mL polymer solution the following ingredients are used:

1. 1.0 g to 2.0 g sterile 70/30 Biodritin powder
2. Sterile CMRL complete culture medium supplemented with 10% fetal calf serum, L-glutamine, and an antibiotic/artimycotic solution, qsp 22.5 ml
3. 2.5 mL of Sterile FC-43 (perfluorotributylamine) (from Sigma chemical Company), about 5% to 25% of the total volume, advantageously, 5% to 20% of the total volume, such as 10% of the total volume.

The mixture is then sonicated in a sterile hood at 40 watts for an appropriate amount of time until a homogenous emulsion is achieved. The polymer is then ready for use. A control polymer is made in the same fashion without the addition of the FC-43, thus adding 25 mL of CMRL complete to the adequate amount of Biodritin. Using this construction and these concentrations, a series of experiments were performed to test the ability of the polymer as an immune barrier and the ability of the fluorocarbon compound to improve over or eliminate the limitations of encapsulation as the result of hypoxia and lack of nutrients.

Example 2

Partial Protection of Calcium Binding Sites

The total blockage of the calcium sites in the alginate solution would require 6.5 ml of a 4.5 M $CaCl_2$ solution, which is not practical to use. A 4.5 M calcium chloride stock solution was diluted 1:5 and 200 μl portions were added at intervals to the sodium alginate solution. During additions, and thereafter, the solution was vigorously mixed with the aid of a power mixer to completely avoid formation of gel clumps. Eight such additions, plus one, were made, in a total of 1800 μl, corresponding to 1.5 mmol of calcium ions added.

Biodritin preparations can also be made in which the calcium binding sites are blocked to a lesser extent, from 25% to 75% of that described above. This also results in soluble materials, provided the coupling with DVS is not extensive.

In applications where the s-IPN gel is prepared, protection of the calcium binding sites is not necessary, as there is no chemical reaction with the alginate component of Biodritin prior to the gel-forming step.

Example 3

DVS-Coupling Reaction

Keeping the alginate gel with protected calcium binding sites under continuous, vigorous mixing, 25 ml of the CIS solution were added, at which time the solution viscosity decreased. The solution was rapidly homogenized by the vigorous mixing and the coupling reagent, DVS, was added in 10 portions of 0.3 ml each, under continuous mixing at 2–3 min intervals.

When DVS addition was complete the mixture was kept for 2 hours in a water bath at 40° C. At the end of this interval the reaction mixture was slightly purple in color; it was removed from the water bath and left overnight at room temperature.

During the reaction steps, continuous mixing is required, which can be easily achieved with help of an electrical mixer with blades or paddles.

Example 4

Processing and Initial Purification

After reaction is complete, the mixture resembled a mousse. To each 100 ml portion of this material was added 15 ml of 1M NaCl and 5×1 ml portions of a 0.63 M EDTA solution, to remove calcium ions from the "egg-box" sites. Mixing was maintained to facilitate solubilization. A very viscous and brownish solution was finally obtained.

The solution was cooled in an ice-water bath, after which 3×100 ml portions of ice-cold ethanol were slowly added with strong mixing with spatula, to precipitate the product. A white, thread-like, copious precipitate formed; the mixture was left for one hour in the ice-water bath, after which it was centrifuged at 4° C., at 6000 rpm for a minimum of 20 minutes, in 250 ml plastic bottles.

Example 5

Blocking the Remaining Active Vinyl Groups

After discarding the supernatant, the centrifuge bottle was inverted for drainage of excess liquid, the precipitate was taken and pressed between filter papers, using gloved hands. It was, then, suspended in 50 ml 1 M ethanolamine at pH 9.4, to which 1 ml 0.63 M EDTA was also added. As dissolution started, an additional 50 ml ethanolamine solution was added in two equal portions; small clumps were broken with a spatula. The solution was then stirred while heated to about 40° C., when complete solution occurred. The container was closed with parafilm and left overnight at room temperature or, alternatively, kept in a water bath at 40° C. for four hours. A golden-yellow, transparent solution resulted that was transferred to a 2 liter beaker for further treatment.

Example 6

Further Purification

The solution of the preceding step was cooled in an ice-water bath and, after 30 min, 3×100 ml portions of ice-cold ethanol were added with hefty mixing with spatula. A white, fibrous precipitate formed that sedimented easily by gravity. The suspension was kept for 1 hour in an ice-water bath, after which it was centrifuged at 6000 rpm for 20 min at 4° C., as before. The clear supernatant was discarded and the precipitate collected as in EXAMPLE 4 above and dried between filter papers.

This precipitate was re-dissolved in 2×50 ml portions of water for a third ethanol precipitation. The solution was transferred to a 2 liter beaker and cooled to ice-water bath temperature. After slow addition of 3×100 ml portions of ice-cold ethanol a white, fibrous precipitate formed and the mixture was left for one hour in the ice-water bath.

The precipitate was collected after centrifugation carried out exactly as described in this EXAMPLE; it was drained, pressed between filter papers and dissolved, with help of a spatula, in 100 ml water. The final solution was clear, very viscous. It was poured into petri dishes, frozen and freeze-dried.

The dry material obtained after freeze-drying was white, weighing, on the average, 5.9 g for this batch size. It was recovered as brilliant, fibrous sheets that break into flakes. The final material is completely soluble in water or 0.15 M NaCl solution. Solutions in both solvents at the levels of 10 to 30 mg/ml form gel spheres when dripped into an 1% calcium chloride solution.

Example 7

Dehydrothermal Preparation of Biodritin

Sodium alginate and CIS solutions were prepared as in EXAMPLE 1 with the important modification that the solvent for each one was now water. "Egg-box" sites were combined with calcium ions as in Example 2. CIS solution was, then, added to alginate; CIS solution can also be added before the calcium ions addition. A power mixer was used to break any clumps that could have formed at the calcium chloride addition steps. The very viscous final mixture was transferred to petri dishes, frozen and freeze-dried.

The hard, dry cake in the petri dishes was then submitted to the dehydrothermal treatment as follows: the dishes containing the cakes were placed in an electric hood maintained at 102–106 C. and kept there for 24 hours. After this time allowed for reaction, the cakes were left to cool to room temperature and further processed.

At this point an average 6.7 g of cake is obtained; it is reduced to powder and suspended into ~75 ml water to which 5–6 ml 0.63 M EDTA is added to remove calcium from the "egg-box" sites. To 100 ml of the mixture is added 10 ml of 1 M NaCl, to render it 0.1 M in NaCl, and the mixture is gently heated. Coarse lumps that would not dissolve with a spatula are removed and the mixture is centrifuged to remove insolubles. The clear supernatant is purified by ethanol precipitation as described in EXAMPLE 6; a total of 3 re-precipitations are carried out, the first two after addition of 2 ml EDTA to assure complete calcium removal. After the third precipitation the cake is suspended in 75 ml water, gently warmed to facilitate solution. The clear solution obtained is transferred to petri dishes, frozen and freeze-dried. A typical yield for such a batch is 5.6 g of final product.

The resulting powder is easily water soluble at concentrations from 10 to 40 mg/ml water or 0.1 M NaCl; the viscosity is a little less than that of equivalent concentrations of Biodritin prepared by chemical co-polymerization with DVS but microcapsules are formed when the solution is dripped into calcium chloride.

Example 8

Preparation of Biodritin-poly-L-Lysine Microcapsules

Stock solutions of Biodritin heteropolysaccharide were prepared at 10, 15, 20 mg/ml (DVS polymerized Biodritin) or 30 mg/ml (DHT Biodritin) in 0.15 M NaCl, at room temperature. Dissolution is rapid and easy. The Biodritin heteropolysaccharide solution was dripped from a syringe into a 1.1% $CaCl_2$ solution, with mild agitation, from a height of about 15 cm, forming beads. The beads were left to mature for different time intervals in the calcium chloride solution, from 5 to 40 min and were, then, processed as described by Sun et al (1984).

i-Briefly, beads are washed, successively in 0.1% CHES (cyclohexyl-ethane sulfonic acid) and 1.1% calcium chloride; they are then treated for 6 min with a 0.5% poly-L-lysine solution, in order to form a capsule of Biodritin-poly-lysine complexes at the bead surface.

ii-The beads are, then, washed in 0.1% CHES, 1.1% calcium chloride and 0.15 M NaCl, in this order; each washing lasts 2 minutes.

iii-An outer coating of Biodritin is now applied by incubation of the capsules with a 0.03% Biodritin heteropolysaccharide solution for 4 minutes, after which the capsules are extensively washed in 0.15 M NaCl. They are stored in 0.15 M NaCl until used.

In this Example no cells were encapsulated; the microcapsules contained only Biodritin-calcium gel and the outside coatings. Pure microcapsules are used to investigate their biocompatibility in animal experiments. The external diameter of the microcapsules prepared in this EXAMPLE was 4–5 mm but, using devices where a coaxial air stream flows around the syringe needle tip, much smaller microcapsules can be prepared, as is known to those versed in this field.

Example 9

Preparation of Biodritin as a s-IPN Physical Gel

In this Example solutions were prepared having the following concentrations of components: solvent was 0.15 M sodium chloride; the alginate concentration was fixed at 3.0% and the CIS concentrations used were 1.5%, 3% and 6%, respectively, giving CIS/alginate ratios by weight of 0.5:1, 1:1 and 2:1. The semi-interpenetrating polymer network was prepared in bead form by dropping each of these solutions into a solution of calcium chloride at 1.1%, as described above.

Beads were formed from a 20 gauge syringe needle, at a rate of 1 ml/min (peristaltic pump); this needle was inserted into a larger one linked to an air pump so that air could be blown around the dropping needle in order to form microbeads, by fractionation of the out-flowing liquid column, that dropped into a calcium chloride solution. A typical preparation consisted of forming beads from 3 ml of each solution, received in 30 ml 0.15 M NaCl in a small beaker. Immediately thereafter the beads were transferred to a 50 ml centrifuge tube, where they were gently mixed with the calcium solution for 10 minutes. In this step the periods can vary from a few minutes to much longer ones, as 40 min, for example, depending on the extent of gelling that is desired.

After this period the beads are centrifuged off at low force (1000 rpm, 3 min), transferred to a 15 ml centrifuge tube and washed with 0.15 M NaCl. A washing sequence as described in Example 8 was applied. A poly-lysine capsule can be applied to the beads, exactly as described above.

Biodritin beads of the s-IPN type were tested for stability, without the poly-lysine capsule, by incubation for 140 hours at room temperature, in 0.15 M NaCl. Analysis of CIS and alginate leakage, made by ultra-violet spectrophotometry at 204 and 215 nm, revealed that only 6% of the total alginate in the beads leaked within the first 50hours for the beads containing 6% CIS, about 4% alginate leaked from the beads with 3% CIS, and ca. 1% leaked from beads with 1.5% CIS, approximately the same leakage observed with alginate control beads. The leakage of CIS, on the other hand, was minimal, in all cases, less than 1%. After this period, the beads were further washed by daily exchanges of 0.15 M NaCl. The leaked amounts decreased and reached zero for all beads by the third exchange, i.e., after 72 hours. These data demonstrate that beads formed by s-IPN are stable and keep their composition after gelling. The beads formed in this Example had an average diameter of 550 µm.

Example 10 s-IPN Gel formed from a Mixture of DVS-CIS-Crosslinked Biodritin and Added CIS A Biodritin solution at 2% (w/v) was prepared in 0.15 M NaCl. The Biodritin powder preparation used had a DVS-cross-linked CIS content of ca 2% by weight, which was raised to 15% by addition of CIS. The final solution, thus, had a composition of 2.0% alginate and 0.3% CIS, on a w/v basis. Beads were prepared by dropping this solution into 1.1% calcium chloride solution, followed by 40 min incubation in the same solution. Additional treatment included formation of a poly-L-lysine capsule, further layered with Biodritin, and washing as described in Example 8. Beads and capsules prepared in this way have identical properties to beads of similar composition prepared from alginate and CIS as in Example 9. They can be treated exactly as the beads described in the next Examples.

Example 11

Sterilization of Microcapsules

In addition to the possibility of sterilizing the Biodritin heteropolysaccharide solution, as well all other solutions used in the capsule preparation by membrane filtration before the gelation step, Biodritin microcapsules can also be sterilized by treatment with 70% (v/v) isopropanol in 0.15 M NaCl. Thus, Biodritin microcapsules were successively treated by Isopropanol/0.15 M NaCl solution of increasing isopropanol concentrations, as follows: 25%, 50% and 70%, all by volume. The first two treatments were applied for 30 min each, to allow slow dehydration of the capsules by the increasing concentrations of isopropanol. When submitted to 70% isopropanol, the microcapsules were left for up to 4 days at room temperature.

Under these conditions, they shrunk to about one-half the initial diameter, presenting wrinkles on the surface. When re-hydrated 4 days later, by decreasing concentrations of isopropanol, in the reverse order, as above, until 0.15 M NaCl was attained, they recovered the original spherical form, without shape deformations, breaks or peeling of the outer layer. The surface examination was done with help of a loupe with varying degrees of magnification.

Differently from this, microcapsules prepared with alginate alone treated the same way and in parallel experiments, shrunk to ⅓ the original volume and did not recover the initial spherical shape. Most became ellipsoids of revolution, with intact surfaces showing wrinkles that did not disappear with time.

Microcapsules treated as in EXAMPLES 8 and 9 were also implanted into mice to test their biocompatibility.

Example 12

Intactness of the Outer Microcapsule Membrane (Biodritin/Poly-Lysine/Biodritin)

The preservation of the outer membrane after sterilization and re-hydration was tested by dissolving a considerable part of the gel in the interior of the microcapsules by treatment with 0.050 M sodium citrate.

Microcapsules were incubated with sodium citrate at room temperature for varying times while observed under a loupe at high magnification. Depending on the capsule size, the time course of events changes but, for a group of larger microcapsules the following results were obtained: after ~10 min, the central core was surrounded by a narrow, very transparent zone, the latter limited by the external membrane.

At 30 min observation, the solubilization of the Biodritin gel by calcium removal by citrate reached about 50% of the capsule diameter; the outer membrane was intact. Mixing the microcapsule suspension by rotation of the flask makes possible to observe the undulating movement of the intact external membrane, also indicating that it is permeable, allowing fluid to move in and out.

Lacking the support of the subjacent gel structure, dissolved by action of citrate, the membrane can be broken by strong aspiration with a pipette.

Example 13

Microcapsule Staining with Alcian Blue

Alcian Blue is a well known stain for chondroitin sulfate (Turnbull, 1993); we found that it also stains alginate, although with less intensity. Microcapsules were stained in 0.5% Alcian Blue in 2% acetic acid, for 20 min; de-staining was in 2% acetic acid, in repeated washings. Biodritin microcapsules give a deeper blue than alginate capsules, as expected. When Biodritin microcapsules prepared as in EXAMPLE 8, are cut in half and stained, the interior of the capsules stains more intensively than the outside, indicating that the external membrane has an effect on the stain diffusion to the capsule interior.

Example 14

Preparation of Structured "Spaghetti"-like Cylinders of Biodritin for Cell and Tissue Implantation A new use of the Biodritin invention is in the preparation of structured spaghetti-like cylinders to contain cells or tissues for implantation, itself an invention to be described for the first time herein, called Biodritin spaghetti. These Biodritin spaghetti are called "structured" because the thin gel cylinder that receives the name spaghetti has an interior structure formed by a string of sewing cotton line or, alternatively, of surgical suture line. The cotton line has a multitude of very fine lateral extensions, as short branches in a long caulis, that spring from the line surface and are embedded into the gel. The surgical suture does not have such branches, but they can be created by scratching the surface of the line with a knife blade, before sterilizing. These lateral extensions of the central line core provide additional area for adhesion between the gel matrix and the central core, reinforcing the structure in a way similar to the iron wires in concrete.

Structured Biodritin spaghetti are prepared as follows:

1) A sterilized cotton sewing line, size 50 or thinner is inserted into a 10 to 20 cm sterile polyethylene catheter of the desired diameter—usually size 60, but size 90 can be used with thinner lines—up to the point where the line reaches the needle, itself connected to a syringe. A surgical suture line can be used in place of the cotton line, with equivalent results. The line should extend beyond the free end of the catheter tubing for 4 to 5 cm, so that in can be handled, anchored or restrained later on in the process (see FIG. 2A).

2) A Biodritin heteropolysaccharide solution of desired concentration, between 0.5 and 3.0%, for example, in the required solvent (saline, culture medium, or Hank's medium), and containing the cell or tissue preparation desired, is introduced into the catheter tubing by syringe aspiration through the catheter, with the line in place. After a given length of the catheter is filled with the solution the catheter tip and the line extension are briefly rinsed with solvent and the set up is ready for spaghetti formation.

3) A structured spaghetti is formed as follows: the catheter filled with Biodritin heteropolysaccharide solution containing cells and connected to the syringe is quickly placed into a calcium chloride solution in a large petri dish or shallow tray and the syringe plunger is pressed, as the catheter is continuously moved forward in the calcium chloride solution. As the Biodritin heteropolysaccharide solution exits the catheter, it enters into immediate contact with calcium ions and instantly forms a cylindrical gel around the cotton line or surgical line. When all the Biodritin heteropolysaccharide solution in the catheter is expelled by the syringe, one is left with a cylindrical gel formed around the line, whose extension is dictated by the amount of Biodritin heteropolysaccharide solution originally in the catheter. At each end of the Biodritin gel there is a continuous piece of line that is now used to hold the gel cylinder during further processing.

4) The Biodritin spaghetti is now left in the calcium chloride solution for a given period of time to strengthen the gel; this period varies according to the type of gel desired, and ranges from 5 to 40 minutes. After the incubation with calcium ions the Biodritin spaghetti are treated exactly as under EXAMPLE 8, to form a Biodritin-poly-L-Lysine membrane covering the spaghetti surface area. This external Biodritin/poly-lysine/Biodritin membrane helps to support the gel and controls permeability according to molecular size.

5) When islets of Langerhans or other cells or tissue are suspended in the Biodritin spaghetti, they distribute themselves in the double cylindrical space contained within the limits of the cotton or surgical line surface, in the inside, and the Biodritin/poly-lysine/Biodritin membrane, in the outside, as shown in FIG. 2A. The number of islets contained per unit cylindrical volume can be controlled by the islet suspension prepared originally in the Biodritin solution. The biocompatible Biodritin gel structure that forms the bulk of the spaghetti supports the islets away from each other and prevents that they clump together, thereby avoiding central necrosis in islets aggregates.

6) The Biodritin spaghetti, with the line extensions at each end, may be implanted individually or can be tied together by the line ends before implantation, as shown in FIG. 2B. In this way, a much larger mass of cells may be implanted, in a rather limited space, but under conditions that preserve the individual spaghetti.

7) Another embodiment of the present invention is that a group of Biodritin spaghetti strings with cells, tied together as in FIG. 3B, can be placed inside a porous, protective and biocompatible external cylinder initially prepared from veins or arteries of an animal or from the recipient himself. Once attached within such a biocompatible container, to form a sort of living tissue cartridge, the Biodritin spaghetti strings can be implanted into a patient. A possible and interesting alternative proposed in this invention is through the umbilical scar in such a way that, eventually, replacement cartridges may be exchanged using rather simple surgical technique.

8) Under the preparation conditions described above, a Biodritin spaghetti of gel length equal to 10 cm would have the following approximate dimensions (FIG. 4): A) gel length—100 mm; B) total internal diameter—0.76 mm; C) cotton line diameter—0.20 mm; D) thickness of Biodritin gel cylinder(B-C)—0.50 mm; volume of Biodritin gel—42.2 mm$^3$, or 4.22 mm$^3$ per linear centimeter length.

Example 15

Animal Implants of Biodritin Microcapsules: Biocompatibility

Biodritin microcapsules of 4–5 mm diameter were implanted intraperitoneally in mice, 3 capsules per mouse, 2 mice per group, following standard surgical procedures and approved protocols.

After one week, one month and three months post-implantation periods the capsules were removed from the animals. The week-long implanted capsules were found to be free in the peritoneal cavity, clean and with no adherences; no inflammatory reaction could be observed in or around the site where they were found.

Similar results were found with the microcapsules that stayed for one month or three months intraperitoneally in mice. The capsules showed a clean, brilliant surface, free of any adherences. As with the week-long experiments, no inflammatory reaction was noticed. FIG. 4 in U.S. Ser. No. 08/877,682 shows a capsule removed from a mouse after three months intraperitoneal implantation. Histological study of the preparations fully supported the conclusion: no cells were found on the beads surface after intraperitoneal implantation for eight days, one month and three months.

Thus, the biocompatibility of this novel material was established, as expected from the ubiquitousness of chondroitin sulfate in the animal kingdom and from its demonstrated inherent non-immunogenicity.

Example 16

Surgical Biodritin Paint or Spray for Suture Protection

In another embodiment of the present invention, a 0.8 to 1.5% (w/v) Biodritin heteropolysaccharide solution in saline is painted on and around a surgical suture; immediately thereafter a 1% (w/v) calcium chloride solution is briefly sprayed as a mist over the painted area. There immediately forms a Biodritin gel over the painted area that protects it from invading cells or from adhering to adjoining tissue. This has important applications in abdominal surgeries, where undesired adherences may form after surgical procedures. As an alternative mode of application, the Biodritin heteropolysaccharide solution can be sprayed over and around the suture, followed by spraying of the calcium chloride solution to form the Biodritin gel.

A third manner of Biodritin application is to mix the Biodritin heteropolysaccharide solution with an insoluble calcium salt, such as tricalcium citrate, forming an uniform suspension of the calcium salt and, immediately before application, mixing this with an aqueous solution of the δ-lactone of gluconic acid, which slowly hydrolyzes to gluconic acid, which dissolves the calcium ions from the citrate, thereby forming the Biodritin gel in situ. This formulation is called "internal gelation" and has been employed to encapsulate microbial cells by Johansen and Fink (1988). To perform this formulation the following proportions are recommended: to each 8 ml of Biodritin heteropolysaccharide solution of adequate concentration (2.5%, for example) add 1 ml of a tricalcium citrate solution (11.4 mg/ml) and, finally, 1 ml of glucono-lactone (10 mg/ml). Upon addition of the glucono-lactone the solubilization of calcium oind takes place in minutes, when the gel starts forming. This is the preferred embodiment of this application.

Additional examples are also presented incorporating the perfluorinated substances in the Biodritin polymer formulation. Specifically, the experiments were broken into three basic premises: First, the ability of FC-43, or for that matter, any perfluorohydrocarbon derivative, to allow for increased tissue density in encapsulation devices. Second, the effect that FC-43, or any perfluorohydrocarbon derivative included in the polymer matrix, has on the overall health of encapsulated cells and tissues. Third, the ability to reverse diabetes in animal subjects using both control and perfluorinated encapsulation devices.

Example 17

The Ability of FC-43 and Any Perfluorohydrocarbon Derivative for Increased Tissue Density in Encapsulation Devices The first experiment addressed the first two premises. Eighty thousand (80,000) human islet equivalents (IEQ) were split into two groups of 40,000 human islet equivalents. Each group was encapsulated in a polymer slab, the first a control solution of 3% Biodritin., the second a 3% Biodritin solution supplemented with 2% FC-43. The polymer mixtures were made in the following way: 0.75 g. of sterile 70/30 Biodritin powder (See Example 1) was added to either 25 mL of sterile CMRL complete culture medium for the controls, or to 24.5 mL of sterile CMRL complete medium with 0.5 mL of sterile FC-43, which was then sonicated The polymer slabs were formed by extruding the islet/polymer mixture into a dialysis tube with one end clamped, clamping the other end, and then submerging the entire tubing in 1.5% calcium chloride solution made in distilled water. The tube was conformed to approximate dimensions of 10 mm width by 3 mm height, by 20 mm length. This means a 5–7 fold increase above the allowable device thickness to date. Based on the number of islets encapsulated in the slab, the tissue density was calculated to be between 22–25%, also much greater than the previously established standards. The slabs were left in culture flasks with 50 mL of CMRL complete, which was changed every other day, for two weeks at 37° C. Similarly, a flask of control, non-encapsulated islets was also kept under the same culture conditions.

By day 5, all of the control islets were dead with only the cellular remains left in the flask. Staining was attempted with dithizone, a viability stain for islets turning the insulin-zinc granules in functioning islets a bright red, with no positive results. Samples from the control polymer slab and the experimental perfluorinated slabs at days 7 and 14 were collected and analyzed. At this point the experiment was terminated. The results were encouraging. The control polymer slabs presented the usual central necrosis in the encapsulated islets, although some cells on the periphery of the polymer slabs did show acceptable cell morphology. However, in the core of the slab, the area where hypoxia and anoxia are at the greatest levels, there were no cells alive, merely holes in polymer where the cells had once been located. Staining with Hematoxylin and Eosin revealed some viable cells on the periphery and antibody staining for insulin showed weak staining in some of these peripheral islets. This was essentially the same for both time points, day 7 and day 14.

The experimental slabs with FC-43 presented astonishing findings. The islets within the slab, at both day 7 and day 14, were virtually free of central necrosis, morphologically they were healthy and structurally sound, and in the core of the slab, the most oxygen deficient region of the polymer matrix, there were islets that stained well with Hematoxylin and Eosin. (FIG. 1). As well, antibody staining for insulin was sweaker. The hypothesis that the use of the polymer along with the perfluorohydrocarbon derivative could improve tissue loading limits while maintaining islet integrity was confirmed. In the present case we reached tissue density level of about 20% v/v, a value impossible to sustain under conditions used until this invention was put to test. Our invention that a combination of our polymer, Biodritin, and a perfluorocompound derivative in the proper mixture can be used to encapsulate, in any device geometry, any cell or tissue type with beneficial viability results is therefore demonstrated for islets of Langerhans in polyhedral slabs.

Example 18

The Effect of FC-43, or Any Perfluorohydrocarbon Derivative Including in the Polymer Matrix, Has on the Overall Health of Encapsulated Cells and Tissues This experiment involved the transplant of Biodritin microcapsules of 500–600 micrometers in diameter containing islet cells. The capsules were made of 4% Biodritin 70/30 (See Example 1) with and without 10% (v/v) FC-43. The capsules were made by an air jet needle droplet generator. The polymer/islet matrix is drawn by a peristaltic pump through PEG tubing into a droplet generator. Room air is pumped into one side of the generator using an air pump. As polymer droplets form at the tip of the needle, they are extruded by the air into a beaker containing 100 mL of 1.5% Calcium Chloride solution. The beads sit in the calcium chloride for 10 minutes, then they are washed twice in 0.15 M NaCl for two minutes. Next, they are washed twice in 0.15M NaCl for two minutes and placed in a culture flask with 50 mL of CMRL complete overnight before transplant. The next day, they are aliquotted into equal volumes of beads depending on the number of animal transplant recipients. Statistically, we have found that there is an average of 5–6 islet particles per capsule, so knowing the volume of the capsules, we can deduce the number of capsules and thus, the number of islet particles implanted.

Figure 2:
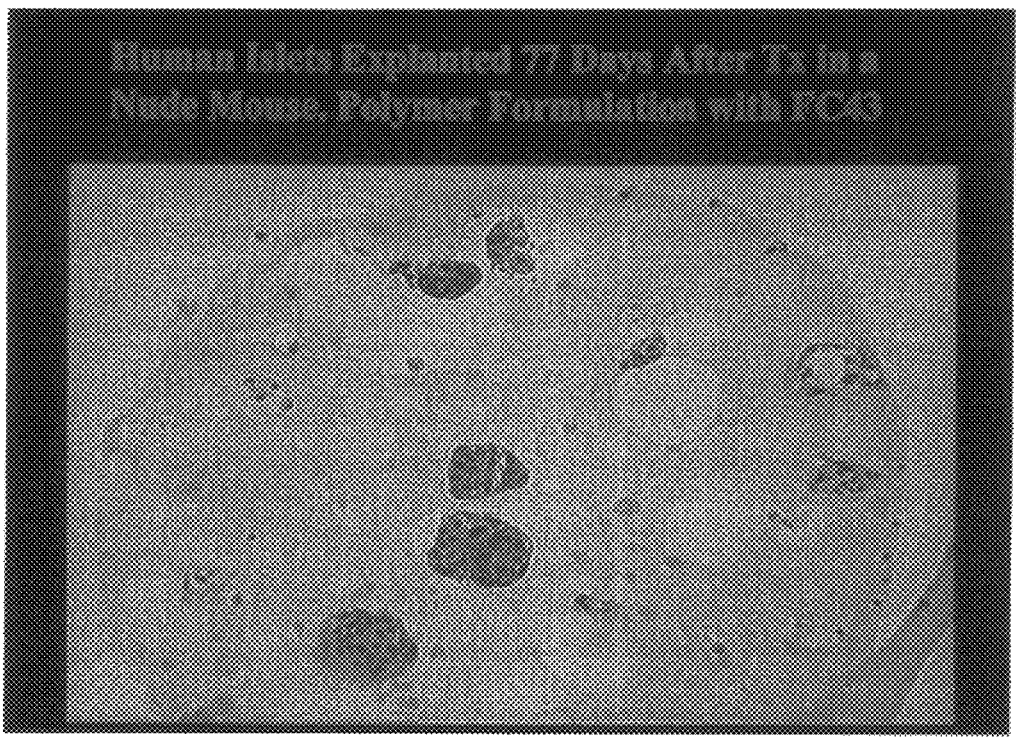
FIG. 2 shows a human islet explanted 77 days after transplant in a nude mouse having polymer formulation with FC43. Specifically, it shows a histological pattern of human islets in microcapsules of Biodritin. Thirty five hundred human islets IEQ's were microencapsulated and transplanted intraperitoneally in NUDE mice. After 77 days of euglycemia in the animals, the microcapsules were explanted for study. FC-43 as in FIG. 1.

We have transplanted 8 diabetic athymic nude mice (diabetes induced by streptozotocin). The first two were transplanted with 3500 human islet equivalents each and the next group of six with 700 rat islet equivalents each. In each group, half of the animals received beads with 10% (v/v) FC-43 and the others received control capsules without FC-43. All eight animals remained normoglycemic, two for 77 days, when the experiment was scheduled to be terminated. They all regained body weight to the normal level of 22–23 g, did not suffer from polyuria, and, to the eye, appeared healthy. The one difference that can be seen between the capsules containing FC-43 and those without it is that the perfluorinated compound-containing capsules seem to maintain a much tighter glycemic control than those without the FC-43. FIG. 2 shows the histological aspect of a capsule containing FC-43 and islets removed after 77 days. Observe that there are at least 6 well structured islets in the slide, that they stain normally, even those closer to the center of the device, and that there are no cell adhesions to the micro-capsule.

Example 19

The Ability to Reverse Diabetes in Animal Subjects Using Both Control and Perfluorinated Encapsulation Devices Our next series of experiments was in an autoimmune diabetic model, non-obese, diabetic mice (NOD mice). One of the discoveries along the path of research in accordance with the present invention was that the perfluorohydrocarbon derivatives also have a marked localized immunosuppressive effect on macrophages, PMN's and act to some extent as free radical scavengers.

Figure 3:
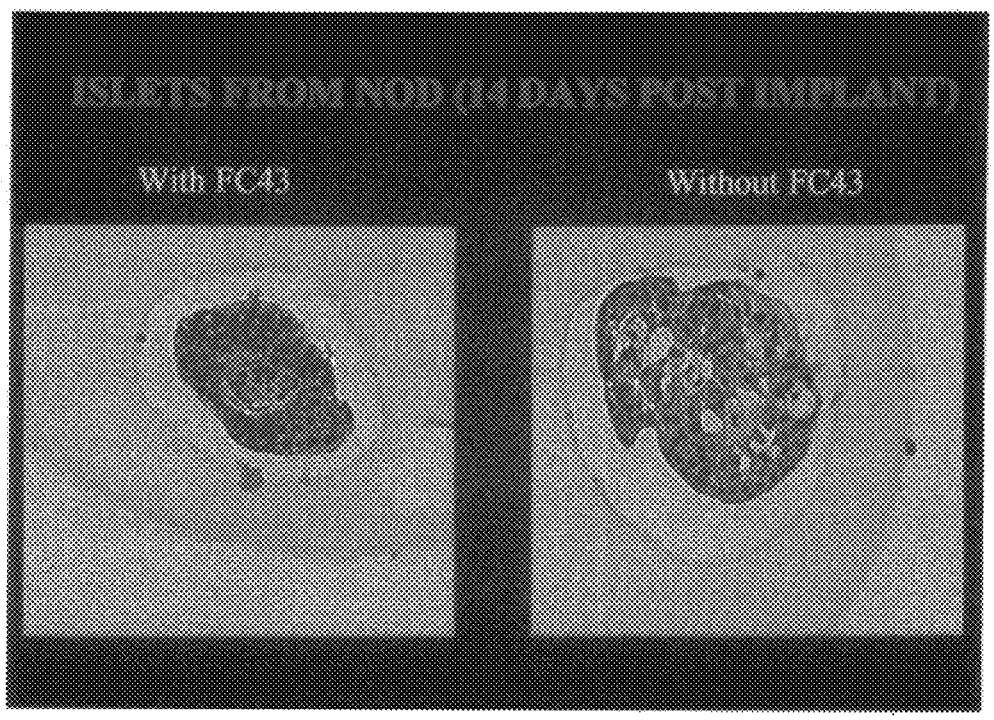
FIG. 3 shows islets from NOD (14 days post implant). Specifically, it shows a histological pattern of rat islets microencapsulated and implanted in non-obese, diabetic (NOD) mice. Fifteen hundred rat islets IEQ's were microencapsulated in Biodritin and implanted intraperitoneally in the NOD mice. Explant took place on day 14. FC-43 as in FIG. 1.

Islets were microencapsulated in Biodritin containing 10% v/v FC-43 and implanted into NOD animals. Control microcapsules contained Biodritin without FC-43 and islets. Diabetes control occurred at the second day post-implant. At day 14 post-implantation the animals were sacrificed and histological examination of the microcapsules was carried out. The islets in capsules containing FC-43 had a much better organized structure, basically without areas of necrosis, whereas those recovered from control capsules, without FC-43 displayed the well known features of central and zonal necrosis, evidenced by areas lacking cells within the islet structure. FIG. 3 illustrates these findings and, again, emphasizes the improvement of islet survival and function when they are encapsulated in polymer media containing a perfluorinated compound.

The uses of the polymer matrix enhanced with fluorocompounds are many. A paste, capsules, flat sheets, spaghetti-like or polyhedral devices containing tissue and a perfluorinated compound in the 10% v/v range will grant cell survival and function over and above the cell densities used in the absence of the perfluoro compound. (One can use the teachings of Examples 2 to 16, in combination with Examples 1 and 17 to 19 to use Biodritin plus perfluorinated compound in any desired forms or setting).

Having thus described in detail the preferred embodiments of the present invention, it is to be understood that the invention defined by the appended claims is not to be limited by particular details set forth in the above descriptions as many apparent variations thereof are possible without departing from the spirit or scope of the present invention.

REFERENCES

1. Scharp, D. W.; Mason, N. S.; Sparks, R. E. Islet Immunoisolation: The use of hybrid artificial organs to prevent tissue rejection. *World J. Surg.* 1984; 8: 221–229.
2. Sun, A. M.; Parisius, W.; MacMorine, H. G.; Sefton, M.; Stone, R. An artificial endocrine pancreas containing cultured islets of Langerhans. *Artif. Organs.* 1980; 19: 541–545.
3. Lanza, R. P. et al. Successful xenotransplantation of a diffusion-based biohybrid artificial pancreas: a study using canine, bovine and porcine islets. *Transplant. Proc.* 1992; 24: 669–671.
4. Lim, F.; Sun, A. M.; Microencapsulated islets as a bioartificial pancreas. *Science.* 1980; 210: 908–910.
5. Chang, T. M. S.; Semipermeable microcapsules. *Science.* 1964; 146:524.
6. Goosen, M. F. A.; O'Shea, G. M.; Gharapetian, H. M.; Chou, S.; Sun, A. M. Optimization of microencapsulation parameters: Semipermeable microcapsules as a bioartificial pancreas. *Biotech. and Bioeng.* 1985; 27: 146–150.
7. King, G. A.; Daugulis, A. J.; Faulkner, P. et al. Alginate-polylysine microcapsules of controlled membrane molecular weight cutoff for mammalian cell culture engineering. *Biotechnol. Prog.* 1987; 3:21.
8. Calafiore, R. Transplantation of microencapsulated pancreatic human islets for therapy in Diabetes Mellitus. *ASAIO Journal.* 1992: 38: 34–37.
9. Kwok, W. Y.; Kiparissides, C.; Yuet, P. et al. Mathematical modelling of protein diffusion in microcapsules: A comparison with experimental results. *Can. J. Chem. Eng.* 1990; 69: 361.
10. Tanaka, H.; Matsumura, M.; Veliky, I. A. Diffusion characteristics of substrates in Ca-alginate gel beads. *Biotech. Bioeng.* 1983; 26: 53.
11. Rafael, E. et al. Microdialysis for in vivo evaluation of permeability of immunoisolation devices. *Transplantation Proceedings.* 1997; 29: 2134–5.
12. Wang, T.; Lacik, I.; Brissova, M.; Anilkumar, A V.; Prokop, A.; Hunkeier, D.; Green, R.; Shahrokhi, K.; Powers, A.; An encapsulation system for the immunoisolation of pancreatic islets. *Nature Biotechnology.* 1997; 15: 358–363.
13. Basta, G.; Osticioli, L.; Rossodivita, M E; Sarchielli, P.; Tortioli, C.; Brunetti, P.; Calafiore, R. Method for the fabrication of coherent microcapusles: A new, potential immunoisolatory barrier for pancreatic islet transplantation. *Diab. Nutr. Metab.* 1995; 8: 105–112.
14. Horcher, A.; Zekom, T.; Siebers, U.; Klock, G.; Schnettler, R.; Arnold, M.; Federlin, K.; Zimmerman, U.; Bretzel, R. G. Insulin relaease from different models of a bioartificial pancreas (microencapsulation versus alginate coating). *Transplantation Proceedings.* 1992; 24: 2950–2951.
15. Colton, C. K. Engineering issues in islet immunoisolation. In: Lanza, P.; Chick, W. L. ed. *Immunoisolation of Pancreatic Islets.* Austin, Tex.: R.G. Landes Publishing Co. 1994; 13.
16. Dionne, K E; Colton, C. K.; Yarmush, M L. Effect of hypoxia on insulin secretion by isolated rat and canine islets of Langerhans. *Diabetes.* 1993; 42: 12–21.
17. Avgoustiniatos, E.; Colton, C. K. Effect of external oxygen mass transfer resistances on viability of imunoisolated tissue. *Ann. NY Acad. Sci.* Dec. 31, 1997; 831: 145–167.
18. Suzuki, K.; Bonner-Weir, S.; Hollister-Lock, J.; Colton, C. K.; Weir, G. Number and volume of islets transplanted in immunobarrier devices. *Cell Transplantation.* 1998; 7 No. 1: 47–52.
19. Dionne, K.; Colton, C. K.; Yarmush, M. Effect of oxygen on isolated pancreatic tissue. *Trans. Am. Soc. Artf. Intern. Organs.* 1989; 35: 739–741.
20. Carlsson, P. O. et al. Measurements of oxygen tension in native and transplanted rat pancreatic islets. *Diabetes.* July 1998;47(7):1027–32.
21. Wu, H.; Avgoustiniatos, E.; Swette, L.; Bonner-Weir, S.; Weir, G. C.; Colton, C. K. In Situ electrochemical oxygen generation with an immunoisolation device. *Ann. NY. Acad. Sci. Jun.* 18, 1999;875:105–25.
22. Riess, J. G. Overview of progress in the fluorocarbon approach to in vivo oxygen delivery. *Biomater Artif Cells Immobilization Biotechnol.* 1992;20(2–4):183–202.
23. Biro, G. P.; Blais, P. Perfluorocarbon blood substitutes. *Crit Rev Oncol Hematol.* 1987;6(4):311–74.
24. Navari, R. M.; Rosenblum, W. I.; Kontos, H. A.; Patterson Jr., J. L. Mass transfer properties of gases in fluorocarbons. *Res. Exp. Med.* 1977; 170: 169–180.
25. Bowman, R. J. Red blood cell substitutes as artificial blood. *Hum. Pathol.* March 1983 14(3): 218–220.
26. Lowe, K. C. Perfluorocarbons as oxygen-transport fluids. *Comp. Biochem. Physiol. A.* 1987; 87(4): 825–838.
27. Rudowski, W. Modem oxygen carriers: state of art 1990. *Mater. Med. Pol.* January–March 1990; 22(1): 3–7.
28. Meinhert H., et al. On the perfluorocarbon emulsions of second generation. *Biomater. Artif Cells Immobilization Biotechnol.* 1992; 20(1): 95–113.
29. Tereshina, E. V., et al. Some aspects of perfluorochemical emulsion's interaction with blood. *Biomater. Artif. Cells Immobilization Biotechnol.* 1992; 20(2–4): 1001–1011.
30. Riess, J. G., et al. Stabilization of Perflubron emulsions with egg yolk phospholipid. *Biomater. Artif. Cells Immobilization Biotechnol.* 1992; 20(2–4): 845–848.
31. Lowe, K. C.; Armstrong, F. Biocompatibility studies with perfluorochemical oxygen carriers. *Biomater. Artif. Cells Immobilization Biotechnol.* 1992; 20(2–4): 993–999.
32. Faithfull, N. S. Oxygen delivery from fluorocarbon emulsions—aspects of convective and diffusive transport. *Biomater. Artif. Cells Immobilization Biotechnol.* 1992; 20(2–): 797–804.
33. Lattes, A., et al. Microemulsions of perfluorinated and semi-fluorinated compounds. *Artif. Cells Blood Substit. Immobil. Biotechnol.* 1994; 22(4): 1007–1018.
34. Spence, R. K., et al. Perfluorocarbons as blood substitutes: the early years. Experience with Flusol DA-20% in the 1980's. *Artif. Cells Blood Substit. Immobil. Biotechnol.* 1994; 22(4): 955–963.
35. Spence, R. K. Perfluorocarbons in the twenty-first century: clinical applications as transfusion alternatives. *Artif. Cells Blood Substit. Immobil. Biotechnol.* 1995; 23(3): 367–380.

36. Shah, N.; Mehra, A. Modeling of oxygen uptake in perfluorocarbon emulsions: some comparisons with uptake by blood. *ASAIO Journal.* 1996; 42: 181–189.
37. Patel, S., et al. Modeling of oxygen transport in blood-perfluorocarbon emulsion mixtures. Part II: tissue oxygenation. *ASAIO Journal.* 1998; 44(3): 157–165.
38. Hoffman, R., et al. Arterial blood gases and brain oxygen availability following infusion of intratracheal fluorocarbon neat liquids. *Biomater. Artif. Cells Immobilization Biotechnol.* 1992; 20(2–4): 1073–1083.
39. Forman, M. B., et al. Role of perfluorochemical emulsions in the treatment of myocardial reperfusion injury. *Am. Heart. J.* November 1992; 124(5): 1347–1357.
40. Jacobs, H. C., et al. Perfluorocarbons in the treatment of respiratory distress syndrome. *Semin. Perinatol.* August 1993; 17(4): 295–302.
41. Holman, W. L., et al. Use of current generation perfluorocarbon emulsions in cardiac surgery. *Artif. Cells Blood Substit. Immobil. Biotechnol.* 1994; 22(4): 979–990.
42. Wada, S., et al. Effects of FC43 emulsion against hyperacute rejection in rodent discordant xenotransplantation. *J. Heart Lung Transplant.* 1995; 14: 968–972.
43. Tutuncu, A. S., et al. Evaluation of lung function after intratracheal perfluorocarbon administration in healthy animals. *Crit. Care Med.* February 1996; 24(2): 274–279.
44. Mosca, R. S., et al. Perfluorocarbon supplementation and postischemic cardiac function. *Surgery.* August 1996; 120(2): 197–204.
45. Sakas, D. E., et al. Perfluorocarbons: recent developments and implications for neurosurgery. *J. Neurosurg.* August 1996; 85(2): 248–254.
46. Ueno, T., et al. Efficacy of perfluorotributylamine/pluronic F-68 stem-emulsion (FC43se) against reperfusion injury in ischemic rabbit lungs. *Transplant Proc.* February–March 1997;29(1–2): 1349–53.
47. Clark, M. C., et al. Perfluorocarbons: future clinical possibilities. *J. Invest. Surg.* November–December 1997; 10(6): 357–365.
48. Goodnaugh L. T., et al. Oxygen carriers as blood substitutes. Past, present, and future. *Clin. Orthop.* December 1998; (357): 89–100.
49. Chiba, T., et al. Transabdominal oxygenation using perfluorocarbons. *J. Pediatr. Surg. May* 1999; 34(5): 895–900; discussion 900–901.
50. Kuroda, Y., et al. A new, simple method for cold storage of the pancreas using perfluorochemical. *Transplantation.* 1988; 46(3): 457–459.
51. Tanioka, Y.; Sutherland, D.; Kuroda, Y.; Gilmore, T. R.; Asaheim, T. C.; Kronson, J. W.; Leone, J. P. Excellence of the two-layer method (University of Wisconsin solution/perfluorochemical) in pancreas preservation before islet isolation. *Surgery.* 1997; 122: 435–442.
52. Urushihara, T., et al. A comparison study of rat pancreas preservation using perfluorochemical and fluorocarbon-emulsion as preservation medium. *Biomater. Artif. Cells Immobilization Biotechnol.* 1992; 20(2–4): 933–937.
53. Ricordi, C.; Lacy, P. E.; Finke, E. H.; Olack, B. J.; Scharp, D. W. Automated method for isolation of human pancreatic islets. *Diabetes.* 1988; 37: 413–420.
54. Virmani, R., et al. Effect of perfluorochemical blood substitutes on human neutrophil function. *Transfusion.* 1984; 24(4): 343–347.
55. Virmani, R., et al. Effects of perfluorochemical on phagocytic function of leukocytes. *Transfusion.* 1983; 23(6): 512–515.
56. Janco, R. L., et al. Perfluorochemical blood substitutes differentially alter human monocyte procoagulant generation and oxidative metabolism. *Transfusion.* 1985; 25(6): 578–582.
57. L. Inverardi, C. Fraker, M. Mares-Guia and C. Ricordi, Islet Encapsulation with a new Polymer and Perfluoro hydrocarbons, Fourth International Congress, The Cell Transplant Society, Montreux, Switzerland, Mar. 21–24, 1999; Cell Transplantation 8, p. 176, Abs.23.
58. S. S. Kong, C. Ricordi and M. Mares-Guia, Evaluation of the Metabolic State of Human Islets by Microcalorimetry, Fourth International Congress, The Cell Transplant Society, Montreux, Switzerland, Mar. 21–24, 1999; Cell Transplantation 8, p. 186, Abs. 63.
59. M. Mares-Guia, Towards Immunoisolation: Islet Cell Encapsulation with Novel Polymer Composition with a Perfluorocarbon Compound, in Symposium on Advanced Therapeutic Alternatives for Diabetes Mellitus, Proceedings of the XIV Annual Meeting of FESBE, Federation of Brazilian Societies of Experimental Biology, Caxambú, MG, Brazil, Aug. 25–28, 1999, p.454–456.

We claim:

1. A composition comprising at least one glycosaminoglycan, at least one perfluorinated compound and at least one alginate, wherein:

the at least one glycosaminoglycan and/or the alginate are cross-linked or polymerized; or the at least one glycosaminoglycan and the alginate are covalently bound; or the at least one glycosaminoglycan and the alginate are cross-linked or polymerized and the at least one glycosaminoglycan and the alginate are covalently bound.

2. The composition claimed in claim 1, wherein the perfluorinated substance is an emulsified perfluorocarbon.

3. A polymer composition as claimed in claim 1 wherein the glycosaminoglycan is CIS.

4. A polymer composition as claimed in claim 1, wherein the perfluorinated substance are perfluorotributylamine (FC-43), perfluorodecalin, perfluorooctyl bromide or bis-perfluorobutyl-ethene.

5. The composition as in any one of claims 1–4 further including cells or tissue.

6. A method for preparing a composition as claimed in claim 1 comprising admixing the perfluorinated compound with the glycosaminoglycan and alginate, wherein prior to or during or after the admixing the at least one glycosaminoglycan and/or the alginate are cross-linked or polymerized; or the at least one glycosaminoglycan and the alginate are covalently bound; or the at least one glycosaminoglycan and the alginate are cross-linked or polymerized and the at least one glycosaminoglycan and the alginate are covalently bound.

7. The method of claim 6 further comprising adding cells or tissue to the composition.

* * * * *